US011692207B2

(12) United States Patent
Orijel et al.

(10) Patent No.: US 11,692,207 B2
(45) Date of Patent: Jul. 4, 2023

(54) ENZYMATIC METHODS FOR BUTANOL PRODUCTION

(71) Applicant: NEWPEK S.A. DE C.V., San Pedro Garza Garcia (MX)

(72) Inventors: Claudio Garibay Orijel, Mexico City (MX); Monica Maria Rios Lozano, Mexico City (MX); Jessica Valeria Guerrero Torres, Ecatepec de Morelos (MX); Ivan Alejandro de la Pena Mireles, Monterrey (MX); Jose Raul Ivan Garza Rodriguez, Monterrey (MX)

(73) Assignee: NEWPEK S.A. DE C.V., Nuevo Leon (MX)

( * ) Notice: Subject to any disclaimer, the term of this patent is extended or adjusted under 35 U.S.C. 154(b) by 883 days.

(21) Appl. No.: 16/098,614

(22) PCT Filed: May 5, 2016

(86) PCT No.: PCT/IB2016/000903
§ 371 (c)(1),
(2) Date: Nov. 2, 2018

(87) PCT Pub. No.: WO2017/191483
PCT Pub. Date: Nov. 9, 2017

(65) Prior Publication Data
US 2021/0222209 A1    Jul. 22, 2021

(51) Int. Cl.
*C12P 7/16*    (2006.01)
(52) U.S. Cl.
CPC ......... *C12P 7/16* (2013.01); *C12Y 101/01027* (2013.01); *C12Y 101/01028* (2013.01);
(Continued)

(58) Field of Classification Search
CPC ............... C12P 7/16; C12Y 101/01027; C12Y 101/01028; C12Y 102/01051;
(Continued)

(56) References Cited

U.S. PATENT DOCUMENTS 8,735,651 B2   5/2014   Lee
9,238,801 B2   1/2016   Li et al.
(Continued)

FOREIGN PATENT DOCUMENTS

DE        40 20 406 A1      1/1992
WO    WO 2013/027282 A1     2/2013

OTHER PUBLICATIONS

Saini, et al. Systematic engineering of the central metabolism in *Escherichia coli* for effective production of n-butanol, 2016, Biotechnology for Biofuels, 9(69): 1-10 (Year: 2016).*
(Continued)

*Primary Examiner* — Louise W Humphrey
*Assistant Examiner* — Anjali Ajit Hirani
(74) *Attorney, Agent, or Firm* — Tucker Ellis LLP

(57) ABSTRACT

A process for producing butanol is provided, involving: A) mixing water, lactate, an enzyme mixture comprising at least one enzyme, at least one cofactor and at least one coenzyme, to prepare a reaction mixture; B) catalytically reacting the reaction mixture for an amount of time sufficient to cause conversion of lactate into butanol; and wherein the conversion of lactate into butanol in B) is associated with a regeneration system of NAD (P)$^+$/NAD (P) H and/or acetyl-CoA/CoA.

22 Claims, 4 Drawing Sheets

(52) U.S. Cl.
CPC ............ *C12Y 102/01051* (2013.01); *C12Y 102/04001* (2013.01); *C12Y 108/01004* (2013.01); *C12Y 203/01012* (2013.01)

(58) Field of Classification Search
CPC .... C12Y 102/04001; C12Y 108/01004; C12Y 203/01012; C12Y 103/01086; C12Y 103/01044; C12Y 102/01057; C10L 1/02; Y02E 50/10
See application file for complete search history.

(56) References Cited

U.S. PATENT DOCUMENTS

| | | |
|---|---|---|
| 2010/0081183 A1 | 4/2010 | Paul et al. |
| 2013/0189745 A1 | 7/2013 | Schwarz et al. |
| 2014/0142352 A1 | 5/2014 | Dauner et al. |
| 2014/0018691 A1 | 7/2014 | Maggio-Hall et al. |
| 2014/0186910 A1* | 7/2014 | Maggio-Hall .............................. C12Y 402/01009 435/135 |
| 2014/0377857 A1 | 12/2014 | Liao et al. |
| 2015/0218594 A1* | 8/2015 | Kraus ...................... C12N 9/88 435/146 |

OTHER PUBLICATIONS

Pohanka, M. D-Lactic Acid as a Metabolite: Toxicology, Diagnosis, and Detection, 2020, BioMed Research International, Article ID 3419034, 1-9 (Year: 2020).*

Datta et al. Enzyme immobilization: an overviewon techniques and support materials, 2013, 3 Biotech, 3: 1-9 (Year: 2013).*

Bischoff, K. Optimal Continuous Fermentation Reactor Design, 1966, The Canadian Journal of Chemical Engineering, 281-284 (Year: 1966).*

International Search Report dated Dec. 12, 2016 in PCT/IB2016/000903 filed May 5, 2016.

Tyler P. Korman, et al., "A synthetic biochemistry system for the in vitro production of isoprene from glycolysis intermediates," Protein Science, vol. 23, 2014, pp. 576-585.

Johanna Niemistö, "Towards sustainable and efficient biofuels production. Use of pervaporation in product recovery and purification," Retrieved from the Internet: [URL: http://jultika.oulu.fi/files/isbn9789526203881.pdf], 2014, 24 Pages.

Extended European Search Report dated Nov. 29, 2019, in Patent Application No. 16901046.9, 10 pages.

European Office Action dated Dec. 17, 2019, in Patent Application No. 16901046.9, 1 page.

Oshiro, M. et al., "Efficient conversion of lactic acid to butanol with pH-stat continuous lactic acid and glucose feeding method by *Clostridium saccharoperbutylacetonicum*", Applied Microbiology and Biotechnology, XP019841671, vol. 87, No. 3, May 26, 2010, pp. 1177-1185.

Krutsakorn, B. et al., "In vitro production of n-butanol from glucose", Metabolic Engineering, XP055251985, vol. 20, Sep. 19, 2013, pp. 84-91.

Xu, P. et al., "Biotechnological Routes to Pyruvate Production", Journal of Bioscience and Bioengineering, XP022590028, vol. 105, No. 3, Mar. 1, 2008, pp. 169-175.

Canadian Office Action dated Mar. 2, 2022 in Canadian Patent Application No. 3,021,033, 6 pages.

Examination Report dated Jan. 18, 2022, in European Patent Application No. 16 901 046.9.

Office Action dated Feb. 2, 2023, in corresponding Canadian Patent Application No. 3,021,033.

* cited by examiner

ENZYMATIC METHODS FOR BUTANOL PRODUCTION

BACKGROUND OF THE INVENTION

Field of the Invention

The present invention relates to the field of biotechnology, more particularly to a method for the enzymatic conversion of lactic acid or lactate to butanol coupled to a regeneration system of NAD (P)+/NAD (P) H and regeneration of acetyl-CoA/CoA.

Description of the Related Art

The 4 carbon alcohols such as n-butanol (or simply butanol) and isobutanol are important industrial chemicals, useful as fuel additives, raw materials in the plastics industry, and as extracting agents in the food grade. Each year, because of increased demand, large amounts of these alcohols are produced in the petrochemical industry.

Typically these alcohols can be produced by chemical synthesis or by biological processes. Butanol can be produced chemically by the hydroformylation of propylene, a process wherein propylene is contacted with a catalyst containing rhodium, that allows the hydroformylation of propylene to form butyraldehyde, then the aldehyde is hydrogenated to form butanol, as described in European patent EP1733003B1. Further butanol can be produced biologically, by a metabolic pathway known as fermentation ABE (Jones and Woods, 1986 widely metabolic pathway; and others, 2012). This fermentation pathway is widely used in industry, using the microorganism *Clostridium acetobutylicum*. However, the production of biological butanol has not yet reached production yields that are truly competitive against chemical processes.

Various documents have been found describing the production of butanol by fermentation that use wild-type or genetically modified material which increases the production of butanol, such as *Clostridium acetobutylicum, Saccharomyces, Escherichia coli* and *Pseudomonas*; see for example the following patents or patent applications, US20090155869A1, US20120149080A1, US2011-0236941A1, U.S. Pat. No. 9,096,872B2, CN101952430B, WO2012033334A3, and U.S. Pat. No. 9,005,953B2. The raw material that is described in these patents is generally a carbohydrate, e.g. glucose, sucrose or fructose, as is highlighted in the patents US20120149080A1 and US 20140377825A1. While this technology has been developed, it is important to note that there are deficiencies in the techniques associated with the use of genetically modified organisms to produce butanol, such as:

1.—There must be many living cells to carry out the process quickly; if there is little biomass, the fermentation process becomes very slow. This fact is widely known in the prior technique.

2.—Introducing an exogenous metabolic pathway to an organism involves competing with the metabolism of the organism itself, because the carbon flux is divided between microbial growth and the production of butanol. This prevents the process from reaching values close to the theoretical yields (for example, for the case of glucose, 0.411 grams of n-butanol per gram of glucose). Therefore, to achieve acceptable yields, it is not only enough to express the metabolic pathway for the production of butanol, but the metabolic pathways that compete with the production of butanol must also be modified by removing genes. For example, the genes encoding for enzymes acetate kinase, lactate dehydrogenase and butyrate kinase, among others, have been deleted as described in patents or patent applications WO2013128230A1, US20100136640A1 and CA2665102C.

3.—It is not enough to eliminate genes, sometimes you have to overexpress endogeneous genes and/or exogeneous genes that establish the biochemical pathway of interest and increase yields in the production of butanol. For example, overexpression of the genes crt, bcd and hbd allows greater activity of the enzymes involved in the synthesis of butanol, as described in patent application WO2014135633A1.

4.—It is common and known in the art to remove and/or overexpress genes in many cases back to the metabolically unstable organisms.

Because of this, it is desirable to have a process where there is no interaction or competition or substrates difference and wherein no growth of any microorganism is associated with the process.

In reference to this, the European patent EP2204453B1 claims butanol production enzymatically. However, to carry out this process glucose is used as raw material. This means that at least 5 enzymes are required to convert glucose into pyruvate. In addition to involving various enzymes to produce pyruvate, the EP2204453B1 patent describes in its examples that the operating temperature of the system should be greater than 50° C. This is because the enzymes that generate pyruvate from glucose do not work efficiently at lower temperatures and, additionally, some of the enzymes that convert pyruvate to butanol that operate efficiently at temperatures of 20 to 37° C., generate the enzymes in an incompatible system and, also, some of them lose their activity quickly, as mentioned in different examples throughout the patent, particularly in example 10.

Furthermore EP2700714A1 mentions a very similar scheme to EP2204453B1, but using at least 13 enzymes to carry out the process.

Accordingly, there is needed a process where the production of butanol is made from lactate, a carbon source that is widely available, where the process is carried out enzymatically, in a process where the action of these enzymes regenerates the acceptor molecules and electron donors, so that the process can be continuous and stable for extended periods of time.

SUMMARY OF THE INVENTION

Therefore, an object of the present invention is to provide an enzymatic method for producing butanol from lactate, wherein the production of butanol is coupled with regeneration of NAD (P)+/NAD (P) H and/or regeneration of acetyl-CoA/CoA and where this process is not associated with the growth of a microorganism.

A further object of the present invention is to provide a method in which the production of butanol from lactate coupled with a regeneration system of NAD (P)+/NAD (P) H and/or regeneration of acetyl-CoA/CoA, can be performed in a controlled environment, where any component of the reaction mixture can be recirculated to the process.

Another object of the present invention is to develop a method wherein the regeneration system of NAD (P)+/NAD (P) H and/or regeneration of acetyl-CoA/CoA is coupled with the production of butanol from lactate in a batch process by using free enzymes or immobilized enzymes.

Another object of the present invention is to develop a method wherein the regeneration system of NAD (P)+/NAD (P) H and/or regeneration of acetyl-CoA/CoA is coupled with the production of butanol from lactate in a semicontinuous process by using free enzymes or immobilized enzymes.

Another object of the present invention is to develop a method wherein the regeneration system of NAD (P)+/NAD (P) H and/or regeneration of acetyl-CoA/CoA is coupled with the production of butanol from lactate in a continuous process by using immobilized or free enzymes.

Another object of the present invention is to provide a biofuel or biofuel precursor made by the process of the present invention, and an automotive engine fuel comprising a mixture of hydrocarbons, and the biofuel or biofuel precursor.

These and other objects of the present invention, alone or in combinations, have been satisfied by the discovery of a process for producing butanol, comprising:

A) mixing water, lactate, an enzyme mixture comprising at least one enzyme, at least one cofactor and at least one coenzyme, to prepare a reaction mixture;

B) catalytically reacting the reaction mixture for an amount of time sufficient to cause conversion of lactate into butanol; and wherein the conversion of lactate into butanol in B) is associated with a regeneration system of NAD $(P)^+$/NAD (P) H and/or acetyl-CoA/CoA.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
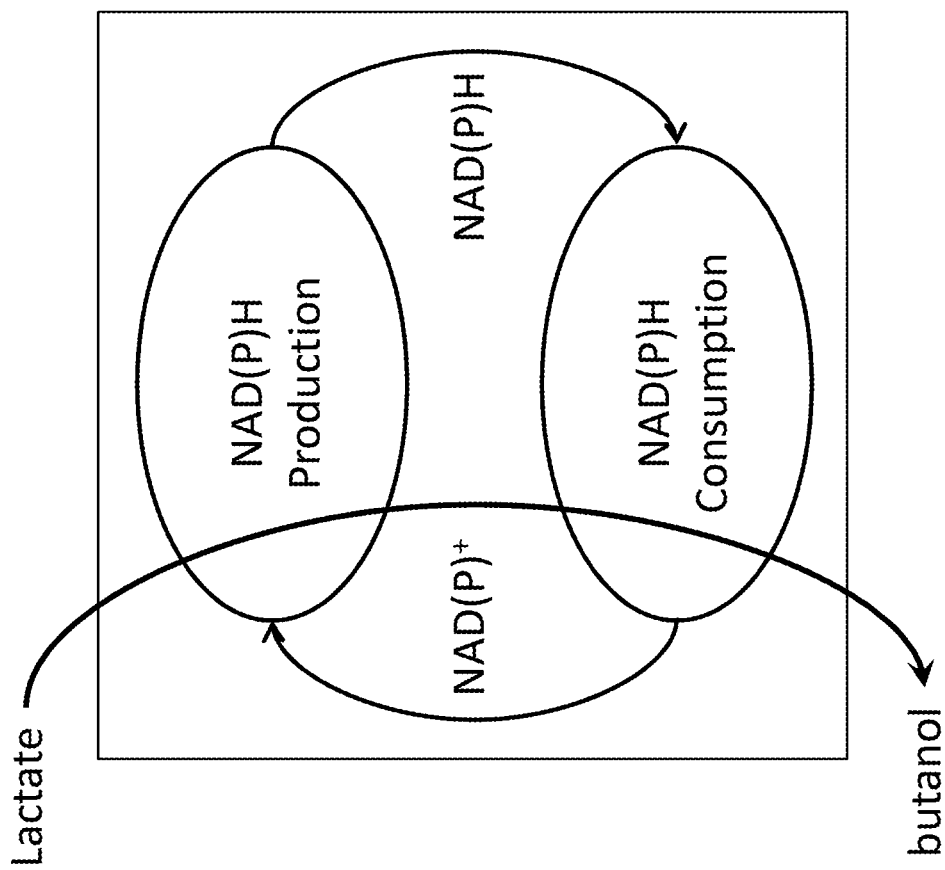
FIG. 1 shows a schematic of a regeneration system NAD (P)+/NAD (P) H coupled with butanol production starting from lactate.

For a clearer understanding of the object of the present invention, the following definitions and abbreviations are established.

The terms "lactic acid", "lactate", "2-hydroxy-propanoic acid" and "α-hydroxypropanoic acid" refers to the same molecule, wherein the said molecule has three carbons and holds the molecular formula $H_3C-CHOH-COOH$ ($C_3H_6O_3$). For purposes of the present invention, the term lactic acid refers to any of the isomers or mixture of isomers reported in the international databases with identification numbers CAS 50-21-5, 79-33-4, 10326-41-7, 598-82-3, which can be L-lactate or D-lactate or a mixture of both in any proportion. Also, for purposes of the present invention, the term "lactate" is equivalent to lactic acid in dissolution conditions and depending on pH lactic acid can be present in its ionic form. Lactate can be obtained in different ways, whether biologically or chemically. Biologically, lactate can be obtained, for example, by the fermentation of organic compounds. Some of the lactate-producing organisms are *Escherichia coli*, *Lactobacillus casei*, *Lactobacillus delbrueckii*, *Lactococcus lactis*, etc. Chemically, the lactate can be obtained, for example from ethanol, sodium cyanide and sulfuric acid, wherein the process ends with a cyanide nucleophilic attack of the carbonyl group of the aldehyde by forming the nitrile of lactic acid in a racemic form. The nitrile is saponified in the presence of water and excess sulfuric acid to give the free lactic acid.

The terms "pyruvate", "pyruvic acid", "2-oxopropanoic acid", "propionic α-keto acid", "pyroracemic acid" and "acetylformic acid" refers to the same molecule, wherein the said molecule has three carbons and holds the molecular formula $CH_3COCOOH$ ($C_3H_4O_3$, CAS: 127-17-3).

The terms "coenzymes" and "Coenzyme" refers to organic compounds, non-protein, necessary for the action of enzymes that are required, for example flavin adenine dinucleotide (FAD), thiamine pyrophosphate (THPP), flavin mononucleotide (FMN), Coenzyme A, etc.

The terms "coenzyme A", "CoA" and "CoA-SH" refers to one molecule widely known in the art, wherein the molecule has twenty one carbon atoms ($C_{21}H_{36}N_7O_{16}P_3S$, CAS: 85-61-0). The CoA is used by cells in all realms and domains, as described in the prior technique, to help carry out enzymatic reactions.

The terms "acetyl-CoA", "acetyl coenzyme A", "ac-CoA", "coenzyme A-acetyl A", "acetyl-S-CoA" and "ac-S-CoA" refers to the same molecule, wherein the said molecule has twenty three carbons and holds the molecular formula $CH_3COSCoA$ ($C_{23}H_{38}N_7O_{17}P_3S$, CAS: 72-89-9).

The terms "acetoacetyl-CoA", "acetoacetyl coenzyme A", "3-acetoacetyl-CoA", "acetoacetyl-S-CoA", "S-acetoacetyl-CoA" and "S-acetoacetylcoenzyme A" refers to a molecule wherein said molecule has twenty five carbons and holds the molecular formula $CH_3COCH_2COSCoA$ ($C_{25}H_{40}N_7O_{18}P_3S$, CAS: 1420-36-6).

The terms "(S)-3-hydroxybutanoyl-CoA", "(S)-3-hydroxybutyryl-CoA", "(3S)-3-hydroxybutanoyl-CoA", "L-3-hydroxybutyryl-CoA", "L(+)-beta-hydroxybutyroyl-CoA", "β-hydroxybutyryl-CoA "and 3-hydroxybutyryl-coenzyme A" refer to a molecule, wherein said molecule has twenty five carbons and holds the molecular formula $CH_3CHOHCH_2COSCoA$ ($C_{25}H_{42}N_7O_{18}P_3S$, CAS: 2871-66-1).

The terms "crotonyl-CoA", "crotonyl-coenzyme A", "2-butenoyl-CoA", "trans-but-2-enoyl-CoA", "but-2-enoyl-CoA", "(E)-but-2-enoyl-CoA" and "crotonyl-S-CoA" refer to a molecule, wherein said molecule has twenty five carbons and holds the molecular formula $CH_3(CH)_2COSCoA$ ($C_{25}H_4ON_7O_{17}P_3S$, CAS: 992-67-6).

The terms "butanoyl-CoA", "butyryl-CoA" and "butyryl-coenzyme A" refer to a molecule, wherein said molecule has twenty five carbons and holds the molecular formula $CH_3(CH_2)_2COSCoA$ ($C_{25}H_{42}N_7O_{17}P_3S$, CAS: 2140-48-9).

The terms "butanal", "butyraldehyde", "1-butanal", "n-butyraldehyde" and "butyric aldehyde" refer to a molecule, wherein said molecule has four carbons and holds the molecular formula $CH_3(CH_2)_2COH$ ($C_4H_8O$, CAS: 123-72-8).

The terms "formic acid", "formate", "methanoic acid", "hydroxycarboxylic acid" refer to a molecule, wherein said molecule has one carbon and holds the molecular formula $HCOOH(CH_2O_2$, CAS: 123-72-8).

The terms "acetolactic-acid 2", "2-acetolactate", "2-Hydroxy-2-methyl-3-oxobutanoic acid", "acetolactate", "acetolactic-acid" and "2-acetyl lactic acid" refer to a molecule, wherein said molecule has five carbons and holds the molecular formula $CH_3COC(CH_3)OHCOOH$ ($C_5H_8O_4$, CAS: 7169-08-3).

The terms "2,3-dihydroxyvalerate", "2,3-dihydroxy-3-methyl butanate," "2,3-dihydroxy-isovalerate," "2,3-dihydroxy-isovaleric acid" refer to a molecule, Wherein Said molecule has five carbons and holds the molecular formula $(CH_3)_2COHCHOHCOOH$ ($C_5H_{10}O_4$ CAS: 1756-18-9).

The terms "ketoisovalerate", "3-methyl-2-oxo-butanoic acid", "2-Oxo isovalerate", "2-Oxoisopentanoate" and "2-cetovaline" refer to a molecule, Wherein Said molecule has five carbons and holds the molecular formula $(CH_3)_2CHCOCOOH$ ($C_5H_8O_3$, CAS: 759-05-7).

The terms "isobutyryl-CoA", "2-methylpropanol-CoA" and "2-methylpropionyl-CoA" refer to a molecule, wherein said molecule has twenty five carbons and holds the molecular formula $(CH_3)_2CHCOSCoA$ ($C_{25}H_{42}N_7O_{17}P_3S$. CAS: 15621-60-0).

The terms "1-butanol", "n-butanol", "n-butyl alcohol", "butyl alcohol", "butanol", "1-hydroxybutane", "butyric alcohol", "butyryl alcohol" and "butan-1-ol" refer to a molecule, wherein said molecule has four carbons and holds the molecular formula $CH_3(CH_2)_3OH$ ($C_4H_{10}O$, CAS: 71-36-3).

The terms "Nicotinamide adenine dinucleotide reduced (NADH)" and "nicotinamide adenine dinucleotide (NAD+)" refers to molecules of the cellular metabolism and are responsible for carrying out reactions of oxidation-reduction or redox.

The terms "reduced nicotinamide adenine dinucleotide phosphate (NADPH)" and "nicotinamide adenine dinucleotide phosphate (NADP+)" refers to molecules of the cellular metabolism and are responsible for carrying out oxidation-reduction reactions or redox.

For purposes of the present invention, the use of the term "NAD (P)+" is equivalent to the terms "NAD+ and/or NADP+ and/or mixture of both," Likewise, the term "NAD (P) H" is equivalent to the terms "NADH and/or NADPH and/or mixture of both", ie, when in a chemical reaction the term NAD (P)+ is recited, the reaction may be carried out either by NAD+ or NADP+ or a mixture of both in an indiscriminate manner. Similarly, when a chemical reaction recites the term NAD (P) H, the reaction can be carried out either NADH or NADPH or a mixture of both in an indiscriminated way.

The term "theoretical yield" refers to the maximum amount of product that can be obtained by a reaction, and is calculated by a stoichiometric equation. This performance will be used as a basis for comparing an experimental reaction with a theoretical amount based on the stoichiometry of the reaction.

The term "experimental performance" refers to the amount of product that is obtained experimentally by a chemical reaction on the amount of substrate consumed.

The term "conversion efficiency" refers to the percentage obtained from the ratio between the experimental and theoretical yield performance, such that the values range from 0 to 100%.

The terms "redox" and "redox reaction" refer to a biochemical reaction that is mediated through the action of an enzyme, wherein a compound is reduced and another is oxidized. Generally, these reactions occur in the cells due to the presence of NAD (P) H (oxidizing agents) and NAD (P)+(reducing agents).

The terms "polypeptide" and "enzyme" refer to a biological molecule consisting of amino acids that is capable of performing a transformation reaction of the starting compound to a final compound, wherein these two compounds are different spatially or molecularly.

The terms "gene" or "genes" refers to biological molecules containing adenine, guanine, cytosine and thymine nucleotide bases or nitrogen compounds. Genes are molecules that transmit information in a cell for the biological synthesis of enzymes.

The term "reactor" refers to a physical space constructed of a suitable material wherein in a controlled manner, a chemical, biochemical, or biological reaction or combinations of these, can be carried out. Different types of reactors can be found in the art. As an example are mentioned continuous stirred tank reactors (CSTR), plug flow reactors (PFR), Fluidized bed reactors (FBR) and packed bed reactors (PBR). Some characteristics of the reactors are: a) corrosion resistance depending on the reaction being carried out; b) its ability to monitor and control operating variables, such as temperature, agitation, pH, dissolved gas concentration, pressure, etc.; c) operating mode, which can be continuous, semicontinuous or batch, the differences between which are readily understood in the art; d) the ability to use different types of catalysts which carry out the reaction, for example, the catalysts may be dissolved or may be trapped or immobilized.

The term "cofactor" refers to inorganic compounds, which are necessary for the action of enzymes required, for example $Mg^{2+}$, $Fe^{2+}$, $Zn^{2+}$, $Na^+$, $K^+$, $Co^{2+}$, $Ni^{2+}$, $Mn^{2+}$, etc., depending on the particular enzyme.

The term "substrate" refers to the molecule on which an enzyme acts. The enzyme can be related and selective for the substrate.

The term "enzyme mix" refers to the set of enzymes found in the same solution, allowing the production of butanol from lactate.

The term "reaction mixture" refers to the group of chemical compounds in aqueous, oily, gaseous or solid phase allowing the catalyzed reactions of a polypeptide or a mixture of polypeptides that can be performed. It comprises "enzyme mix", "cofactors", "coenzymes", "NAD (P)+/ NAD (P) H" and "lactate"

The term "sequential" refers to the orderly transformation of pyruvate to lactate by lactate dehydrogenase enzymes (EC 1.1.1.27 and/or EC 1.1.1.28), of pyruvate to acetyl-CoA by pyruvate dehydrogenase complex (EC 1.2.4.1, EC 2.3.1.12 EC 1.8.1.4, and EC 1.2.1.51), of acetyl-CoA a acetoacetyl-CoA by the enzyme acetoacetyl-CoA thiolase (EC 2.3.1.9), of acetoacetyl-CoA to (S)-3-hydroxybutanoyl-CoA by the enzyme 3-hydroxybutyryl-CoA dehydrogenase (EC 1.1.1.35 and/or EC 1.1.1.157), of (S)-3-hydroxybutanoyl-CoA to crotonyl-CoA by the enzyme (S)-3-hydroxybutanoyl-CoA hydro-lyase (EC 4.2.1.55) and/or enoyl-CoA hydratase (EC 4.2.1.17), of crotonyl-CoA to butanoyl-CoA by the enzyme trans-2-enoyl-CoA reductase (EC 1.3.1.44) and/or butyryl-CoA dehydrogenase (EC 1.3.1.86), of butanoyl-CoA to butanal by the enzyme butanal dehydrogenase (EC 1.2.1.57) and/or acetaldehyde dehydrogenase (EC 1.2.1.10) and of butanal to butanol by the enzyme alcohol dehydrogenase (EC 1.1.1.1 and/or EC 1.1.1.2), using the ABE fermentation metabolic pathway via pyruvate dehydrogenase complex.

The term "sequential" also refers to the orderly transformation of lactate to pyruvate by using lactate dehydrogenase enzymes (EC 1.1.1.27 and/or EC 1.1.1.28), of pyruvate to formate and acetyl CoA by the enzyme formate acetyltransferase (EC 2.3.1.54), of the generation of NADH by enzyme formate oxidoreductase (1.2.1.2 and/or 1.2.1.4), of acetyl-CoA to acetoacetyl-CoA by the enzyme acetoacetyl-CoA thiolase (EC 2.3.1.9), of acetoacetyl-CoA to (S)-3-hydroxybutanoyl-CoA by the enzyme hydroxybutyryl-CoA dehydrogenase (EC 1.1.1.35 and/or EC 1.1.1.157), of (S)-3-hydroxybutanoyl-CoA to crotonyl-CoA by the enzyme (S)-3-hydroxybutanoyl-CoA hydro-lyase (EC 4.2.1.55) and/or enoyl-CoA hydratase (EC 4.2.1.17), of crotonyl-CoA to butanoyl-CoA by the enzymes trans-2-enoyl-CoA reductase (EC 1.3.1.44) and/or butyryl-CoA dehydrogenase (EC 1.3.1.86), of butanoyl-CoA to butanal by the enzyme butanal dehydrogenase (EC 1.2.1.57) and/or acetaldehyde dehydrogenase (EC 1.2.1.10) and of butanal to butanol by the enzyme alcohol dehydrogenase (EC 1.1.1.1 and/or EC 1.1.1.2), using the ABE fermentation metabolic pathway via oxidoreductase format.

The term "sequential" also refers to orderly transformation of lactate to pyruvate by lactate dehydrogenase enzymes (EC 1.1.1.27 and/or EC 1.1.1.28), of pyruvate to 2-acetolactate by the enzyme acetolactate synthase (EC 2.2.1.6), of 2-acetolactate to 2,3-hydroxyvalerate by the enzyme keto acid reductoisomerase (EC 1.1.1.86), of 2,3-dihydroxyvalerate to ketoisovalerate by the enzyme dihydroxyacid dehydratase (EC 4.2.1.9), of ketoisovalerate to isobutyryl-CoA by the enzyme 2-oxoisovalerate dehydrogenase (EC 1.2.1.25 and/or EC 1.2.4.4), of isobutyryl-CoA to butyryl-CoA by the enzyme isobutyryl-CoA mutase (EC 5.4.99.13), of butyryl-CoA to butanal by the enzyme butanal dehydrogenase (EC 1.2.1.57) and/or acetaldehyde dehydrogenase (EC 1.2.1.10) and of butanal to butanol by the enzyme alcohol dehydrogenase (EC 1.1.1.1 and/or EC 1.1.1.2), using the metabolic pathway of ketoacids.

The term "multienzymatic system" refers to a group of enzymes that sequentially transform the lactate into butanol.

The term "elimination of genes" refers to a cleavable procedure of a region of DNA coding for a protein.

The term "exogeneous gene" refers to a region of ADN coding for a protein that is foreign to the organism.

The term "endogeneous gene" refers to a region of ADN coding for a protein found within the organism.

The term "overexpression" refers to increased expression levels of a protein encoded by an endogeneous gene or an exogeneous gene.

The term "regeneration of NAD(P)$^+$/NAD(P)H" refers to the transformation of molecules of NAD(P)$^+$ by molecules of NAD(P)H due to the action of any enzyme that may have this activity, as well as the transformation of molecules of NAD(P)H of molecules of NAD(P)$^+$ due to the action of any enzyme that may have this activity. Such transformations can be found in a single reaction system or several reactions, depending on the process.

The term "regeneration of acetyl-CoA/CoA" refers to the transformation of molecules of acetyl-CoA in molecules CoA due to the action of any enzyme that may have this activity, as well as the transformation of molecules of CoA in molecules acetyl-CoA due to the action of any enzyme that may have this activity. Such transformations can be found in a single reaction system or several reactions, depending on the process.

The term "free enzyme" refers to an enzyme distributed in a solution.

The term "free enzymes" refers to a group of enzymes distributed in a solution.

The term "support" refers to a solid or semisolid, inert matrix, which preferably does not modify the protein structure, for example activated carbon, zeolite, calcium alginate, silica gel, etc.

The term "immobilized enzyme" refers to the enzyme attached, trapped, absorbed, adsorbed, bound, etc., by any physical or chemical method to a support.

The term "immobilized enzymes" refers to a group of enzymes attached, trapped, absorbed, adsorbed, bound, etc., by any physical or chemical method to a support.

The term "L-lactate dehydrogenase" (EC 1.1.1.27) refers to a polypeptide having catalytic activity, where the catalytic activity is to transform a compound of L-lactate into pyruvate using NAD(P)$^+$. However, there may be another enzyme that is not listed by this group of enzymes that carry out the described reaction, so that enzyme will be considered as an analogue of L-lacate dehydrogenase. Examples of enzymes that can carry out the conversion reaction of L-lactate to pyruvate are described in Table 1. The enzymes described in Table 1 are shown for reference only, since there are databases which can be found more examples of these enzymes, such as in GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 1

Examples of L-lactate dehydrogenase that can be used to transform the L-lactate to pyruvate.

| Name of the gene | Organism |
| --- | --- |
| L-Lactate dehydrogenase APECO1_2404 | *Escherichia coli* APEC 01 |
| L-Lactate dehydrogenase ECS88_4540 | *Escherichia coli* O45: K1: H7 S88 |
| L-lactate dehydrogenase ECOK1_4554 | *Escherichia coli* IHE3034 |
| L-lactate dehydrogenase Ldhal6b | *Mus musculus* |
| L-lactate dehydrogenase Ldha | *Cricetulus griseus* |
| L-lactate dehydrogenase Ldhb | *Pongo abelii* |
| L-lactate dehydrogenase LDHAL6B | *Canis familiaris* |
| L-lactate dehydrogenase IDH1 | *Staphylococcus aureus* subsp. COL *aureus* (MRSA) |
| L-lactate dehydrogenase Ldh | *Corynebacterium glutamicum* K051 |
| L-Lactate dehydrogenase ldh | *Sorangium cellulosum* So ce 56 |
| L-lactate dehydrogenase ldh | *Bacillus subtilis* subsp. *subtilis* 168 |
| Lactate dehydrogenase L-ldh | *Lactococcus lactis* subsp. *lactis* Il1403 |
| L-lactate dehydrogenase AFUA_5G14800 | *Aspergillus fumigatus* |
| L-lactate dehydrogenase Ent638_2002 | *Enterobacter* sp. 638 |
| L-lactate dehydrogenase SPAP_1246 | *Streptococcus pneumoniae* AP200 |

The term "D-lactate dehydrogenase" (EC 1.1.1.28) refers to a polypeptide having catalytic activity, where the catalytic activity is to transform a compound of D-lactate into pyruvate using NAD(P)$^+$. However, there may be another enzyme that is not listed by this group of enzymes that carry out the described reaction, so that enzyme will be considered as an analogue of D-lactate dehydrogenase. Examples of enzymes that can carry out the conversion reaction of D-lactate to pyruvate are described in Table 2. The enzymes described in Table 2 are shown for reference only, since there are databases in which can be found more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 2

Examples of D-lactate dehydrogenase that can be used to transform the D-lactate to pyruvate.

| Gene name | Organism |
|---|---|
| D-Lactate dehydrogenase ldha | Escherichia coli K-12 MG1655 |
| D-Lactate dehydrogenase ldha | Escherichia coli O26: H11 11368 (EHEC) |
| D-Lactate dehydrogenase ldha | Escherichia coli PMV-1 |
| D-Lactate dehydrogenase ldha | Escherichia coli O145: H28 RM13514 (EHEC) |
| D-Lactate dehydrogenase dld | Shigella boydii Sb227 |
| Lactate dehydrogenase D-Spea_0742 | Shewanella pealeana |
| D-Lactate dehydrogenase ldha | Treponema pallidum Fribourg-Blanc |
| D-Lactate dehydrogenase M062_04545 | RP73 Pseudomonas aeruginosa |
| D-Lactate dehydrogenase dld | Acinetobacter sp. ADP1 |
| D-Lactate dehydrogenase PC1_2294 | Pectobacterium carotovorum subsp. carotovorum PC1 |
| D-Lactate dehydrogenase dld | WUE 2594 Neisseria meningitidis (serogroup A) |
| D-Lactate dehydrogenase ldha | Cytophaga hutchinsonii |
| D-Lactate dehydrogenase Plabr_4649 | Planctomyces brasiliensis |
| D-Lactate dehydrogenase Sthe_3421 | sphaerobacter thermophilus |
| D-Lactate dehydrogenase Alfi_3240 | Alistipes finegoldii |

The term "pyruvate dehydrogenase complex" refers to a group of polypeptides (EC 1.2.1.51, EC 1.2.4.1, 2.3.1.12 and 1.8.1.4) that holds catalytic activity, where this catalytic activity is to transform the a compound of pyruvate into acetyl-CoA using $NAD(P)^+$. However, there may be another enzyme that is not cataloged in this set of enzymes that carries out the reaction described, so that enzyme will be considered as an analogue of pyruvate dehydrogenase complex. Examples of enzymes that can carry out the conversion reaction of pyruvate to acetyl-CoA are described in Table 3. Enzymes described in Table 3 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 3

Examples of pyruvate dehydrogenase complex that can be used to transform pyruvate to acetyl-CoA.

| Name of the gene | Organism |
|---|---|
| Pyruvate dehydrogenase b0114 | Escherichia coli K-12 MG1655 |
| Pyruvate dehydrogenase TY21A_00815 | Salmonella enterica subsp. serovar Typhi Ty21a enterica |
| Pyruvate dehydrogenase DR71_379 | Corynebacterium sp. ATCC 6931 |
| Pyruvate dehydrogenase CHLREDRAFT_139515 | Chlamydomonas reinhardtii |
| Pyruvate dehydrogenase ECO103_0115 | Escherichia coli O103: H2 |

TABLE 3-continued

Examples of pyruvate dehydrogenase complex that can be used to transform pyruvate to acetyl-CoA.

| Name of the gene | Organism |
|---|---|
| Pyruvate dehydrogenase LC20_04470 | Yersinia enterocolitica |
| Pyruvate dehydrogenase N297_5189 | Pseudomonas aeruginosa |
| Pyruvate dehydrogenase b0116 | Escherichia coli K-12 MG1655 |
| Pyruvate dehydrogenase HMPREF0538_21877 | Lactobacillus reuteri |

The term "acetoacetyl-CoA thiolase" (EC 2.3.1.9) refers to a polypeptide having catalytic activity, where the catalytic activity is to transform 2 molecules of acetyl-CoA in a molecule of acetoacetyl-CoA. However, there may be another enzyme that is not cataloged in this set of enzymes that carry out the reaction described, so that enzyme will be considered as an analogue of acetoacetyl-CoA thiolase. Examples of enzymes that can carry out the conversion reaction of acetyl-CoA to acetoacetyl-CoA are described in Table 4. The enzymes disclosed in Table 4 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 4

Examples of acetoacetyl-CoA thiolase of which can be used to transform two molecules of acetyl-CoA in 1 molecule of acetoacetyl-CoA.

| Name of the genee | organism |
|---|---|
| Acetyl-CoA thiolase R2866_1623 | Haemophilus influenzae R2866 |
| Acetyl-CoA thiolase EC042_2465 | Escherichia coli O44: H18 042 |
| Acetyl-CoA thiolase XCC1297 | Xanthomonas campestris pv. campestris ATCC 33913 |
| Acetyl-CoA thiolase ES15_0718 | Cronobacter sakazakii ES15 |
| Acetyl-CoA thiolase SSON_2283 | Shigella sonnei Ss046 |
| Acetyl-CoA thiolase HMPREF0462_0751 | Helicobacter pylori 83 |
| Acetyl-CoA thiolase ACIAD2516 | Acinetobacter sp. ADP1 |
| Acetyl-CoA thiolase ECUMN_2562 | Escherichia coli O17: K52: H18 UMN026 |
| Acetyl-CoA thiolase STM14_3646 | Salmonella enterica subsp. enterica serovar typhimurium 14028s |
| Acetyl-CoA thiolase PP_2051 | Pseudomonas putida KT2440 |

The term "3-hydroxyacyl-CoA dehydrogenase" or "3-hidroxybutyryl-CoA dehydrogenase" (EC 1.1.1.35 and/or EC 1.1.1.157) refers to a polypeptide having catalytic activity, where the catalytic activity is to convert acetoacetyl-CoA compound to (S)-3-hydroxybutanoyl-CoA using NAD (P) H. However, there may be another enzyme that is not listed in this group of enzymes that carry out the described reaction, so that enzyme will be considered as an analogue-3-hydroxyacyl CoA dehydrogenase. Examples of enzymes that can carry out the conversion reaction of acetoacetyl-CoA to (S)-3-hydroxybutanoyl-CoA are described in Table 5. The enzymes described in Table 5 are shown for reference only, since there many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 5

Examples of 3-hydroxyacyl CoA dehydrogenase that can be used to transform acetoacetyl-CoA to(S)-3-hydroxybutanoyl-CoA.

| Name of the gene | Organism |
| --- | --- |
| 3-hydroxyacyl-CoA dehydrogenase SEEH1578_05995 | Salmonella enterica subsp. enterica serovar Heidelberg 41578 |
| 3-hydroxyacyl-CoA dehydrogenase ECO103_2805 | Escherichia coli O103:H2 12009 |
| 3-hydroxyacyl-CoA dehydrogenase XALc_1594 | Xanthomonas albilineans |
| 3-hydroxyacyl-CoA dehydrogenase ANI_1_165104 | Aspergillus niger |
| 3-hydroxyacyl-CoA dehydrogenase jk0159 | Corynebacterium jeikeium |
| 3-hydroxyacyl-CoA dehydrogenase A3UG_16295 | Enterobacter cloacae subsp. Dissolvens |
| 3-hydroxyacyl-CoA dehydrogenase SerAS9_0217 | Serratia plymuthica AS9 |
| 3-hydroxyacyl-CoA dehydrogenase ACIAD1690 | Acinetobacter sp. |
| 3-hydroxyacyl-CoA dehydrogenase KPN_01476 | Klebsiella pneumoniae |
| 3-hydroxyacyl-CoA dehydrogenase b1395 | Escherichia coli K-12 MG1655 |

The term "(S)-3-hydroxybutanoyl-CoA hydro-lyase" (EC 4.1.1.55) and "enoyl-CoA hydratase" (EC 4.2.1.17) refers to polypeptides having catalytic activity, where the catalytic activity is to transform a compound of (S)-3-hydroxybutanoyl-CoA into crotonyl-CoA. However, there may be another enzyme that is not cataloged in this set of enzymes that carry out the reaction described, so that enzyme will be considered as an analogue of "(S)-3-hydroxybutanoyl-CoA hydro-lyase and/or enoyl-CoA hydratase. Examples of enzymes that can carry out the conversion reaction of (S)-3-hydroxybutanoyl CoA to crotonyl-CoA are described in Table 6. The enzymes described in Table 6 are shown for reference, since there are many databases where one can find more examples of these enzymes, such as the GeneBank (http://www.ncbi.nlm.nih.gov), the Kyoto Encyclopedia of Genes and Genomes (www.kegg.jp), the Braunschweig Enzyme Database (http://www.brenda-enzymes.org), etc.

TABLE 6

Examples of (S)-3-hydroxybutanoyl-CoA hydro-lyase and/or enoyl-CoA hydratase which can be used to transform the (S)-3-hydroxybutanoyl-CoA to crotonyl-CoA.

| Name of the gene | Organism |
| --- | --- |
| (S)-3-hydroxybutanoyl-CoA hydrolyase M3Q_289 | Acinetobacter baumannii |
| (S)-3-hydroxybutanoyl-CoA hydrolyase M634_03020 | Vibrio parahaemolyticus |
| (S)-3-hydroxybutanoyl-CoA hydrolyase Reut_C6351 | Ralstonia eutropha |
| (S)-3-hydroxybutanoyl-CoA hydrolyase Xaut_2482 | Xanthobacter autotrophicus |
| (S)-3-hydroxybutanoyl-CoA hydrolyase AZL_006240 | Azospirillum sp. B510 |
| enoyl CoA hydratase-AT3GO6860 | Arabidopsis thaliana |
| enoyl CoA hydratase-ECMDS42_1912 | Escherichia coli K-12 MDS42 |

TABLE 6-continued

Examples of (S)-3-hydroxybutanoyl-CoA hydro-lyase and/or enoyl-CoA hydratase which can be used to transform the (S)-3-hydroxybutanoyl-CoA to crotonyl-CoA.

| Name of the gene | Organism |
| --- | --- |
| enoyl CoA hydratase-TY21A_02420 | Salmonella entérica |
| enoyl CoA hydratase-YP_2417 | Yersinia pestis |
| enoyl CoA hydratase-APA22_22590 | Acetobacter |

The terms "trans-2-enoyl-CoA reductase" (EC 1.3.1.44) and "butyryl-CoA dehydrogenase" or "crotonyl Coenzyme A reductase" (EC 1.3.1.86 and/or 1.3.8.1) refers to a polypeptide having catalytic activity, where this catalytic activity is to transform a compound of crotonyl-CoA into butanoyl-CoA using NAD(P)H. However, there may be another enzyme that is not listed in this group of enzymes that carry out the described reaction, so that enzyme will be considered as an analogue of trans-2-enoyl-CoA reductases and/or butyryl-CoA dehydrogenase. Examples of enzymes that can carry out the conversion reaction of crotonyl-CoA to butanoyl-CoA using NAD(P)H are described in Table 7. The enzymes described in Table 7 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 7

Examples of trans-2-enoyl-CoA reductase and butyryl-CoA dehydrogenase which can be used to transform crotonyl-CoA to butanoyl-CoA.

| Name of the gene | Organism |
| --- | --- |
| trans-2-enoyl-CoA reductase YPDSF_3930 | Yersinia pestis |
| trans-2-enoyl-CoA reductase SMWW4_v1c19670 | Serratia marcescens |
| trans-2-enoyl-CoA reductase SMB_G0472 | Clostridium acetobutylicum DSM 1731 |
| trans-2-enoyl-CoA reductase CA_C0462 | Clostridium acetobutylicum ATCC 824 |
| trans-2-enoyl-CoA reductase CPE2074 | Clostridium perfringenes 13 |
| butyryl-CoA Dehydrogenase SGR_1170 | Streptomyces griseus |
| butyryl-CoA Dehydrogenase B446_01590 | Streptomyces collinus |
| butyryl-CoA dehydrogenase AMES_1564 | Amycolatopsis mediterranei S699 |
| butyryl-CoA dehydrogenase KSE_56510 | Kitasatospora setae |
| butyryl-CoA dehydrogenase Afer_0105 | Acidimicrobium ferrooxidans |

The terms "butanal dehydrogenase" (EC 1.2.1.57) and/or "acetaldehyde dehydrogenase (EC 1.2.1.10) refers to a polypeptide having catalytic activity, where this catalytic activity is to transform a compound of butanoyl-CoA into butanal using NAD(P)H. However, there may be another enzyme that is not listed in this group of enzymes that carry out the described reaction, so that enzyme will be considered as an analogue of butanal dehydrogenase and/or acetaldehyde dehydrogenase. Examples of enzymes that can carry out the conversion reaction of butanoyl-CoA to butanal are described in Table 8. The enzymes described in Table 8 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 8

Examples of butanal dehydrogenase and/or acetaldehyde dehydrogenase which can be used to transform el butanoyl-CoA to butanal.

| Name of the gene | Organism |
| --- | --- |
| Acetaldehyde dehydrogenase ECMDS42_0273 | *Escherichia coli* K-12 MDS42 |
| Acetaldehyde dehydrogenase ECSF_0322 | *Escherichia coli* O150: H5 SE15 |
| Acetaldehyde dehydrogenase STY1302 | *Salmonella entérica* |
| Acetaldehyde dehydrogenase SMB_P034 | *Clostridium acetobutylicum* DSM 1731 |
| Acetaldehyde dehydrogenase JDM1_2930 | *Lactobacillus plantarum* JDM1 |

The term "alcohol dehydrogenase" (EC 1.1.1.1 and/or EC 1.1.1.2) refers to a polypeptide having catalytic activity, where this catalytic activity is to transform a compound of butanal into butanol using NAD(P)H. However, there may be another enzyme that is not listed in this group of enzymes that carry out the described reaction, so that enzyme will be considered as an analogue of alcohol dehydrogenase. Examples of enzymes that can carry out the conversion reaction of isobutyraldehyde to butanol using NAD(P)H are described in Table 9. The enzymes described in Table 9 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 9

Examples of alcohol dehydrogenase which can be used to transform butanal to butanol.

| Name of the gene | Organism |
| --- | --- |
| Alcohol dehydrogenase BCG_0198c | *Mycobacterium bovis* |
| Alcohol dehydrogenase AFUA_1G01780 | *Aspergillus fumigatus* |
| Alcohol dehydrogenase LGG_02124 | *Lactobacillus rhamnosus* |
| Alcohol dehydrogenase CKL_0543 | *Clostridium kluyveri* |
| Alcohol dehydrogenase SMB_G3335 | *Clostridium acetobutylicum* DSM 1731 |
| Alcohol dehydrogenase ECMDS42_1036 | *Escherichia coli* K-12 MDS42 |
| Alcohol dehydrogenase SeAG_B1628 | *Salmonella enterica* subsp. *enterica* |
| Alcohol dehydrogenase XC_0320 | *Xanthomonas campestris* |
| Alcohol dehydrogenase BCB4264_A3819 | *Bacillus cereus* B4264 |
| Alcohol dehydrogenase CPE1256 | *Clostridium perfringens* 13 |

The term "pyruvate formate-lyase" or "formate acetyl-transferase" refers to a polypeptide (EC 2.3.1.54) having catalytic activity, where this catalytic activity is to transform a compound of pyruvate into acetyl-CoA and formate. However, there may be another enzyme that is not listed in this group of enzymes that carry out the described reaction, so that enzyme will be considered as an analogue of the enzyme pyruvate formate-lyase. Examples of enzymes that can carry out the conversion reaction of pyruvate to acetyl-CoA are described in Table 10. The enzymes described in Table 10 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 10

Examples of the enzyme pyruvate formate-lyase which can be used to transform pyruvate to acetyl-CoA.

| Name of the genee | Organism |
| --- | --- |
| Pyruvate formate lyase OSTLU_36056 | *Ostreococcus lucimarinus* |
| Pyruvate formate lyase Ot02g06590 | *Ostreococcus tauri* |
| Pyruvate formate lyase Bathy02g04090 | *Bathycoccus Prasinos* |
| Pyruvate formate lyase ybiW | *Escherichia coli* K-12 MG1655 |
| Pyruvate formate lyase ybiW | *Escherichia coli* K-12 W3110 |
| Pyruvate formate lyase | *Streptococcus mutans* strain JC2 |
| Pyruvate formate lyase | *Clostridium pasteurianum* |
| Pyruvate formate lyase | *Chlamydomonas reinhardtii* |

The term "formate dehydrogenase" refers to a polypeptide (EC 1.2.1.43) having catalytic activity where this catalytic activity is to transform a compound of formate to $CO_2$, using a molecule of $NAD(P)^+$. However, there may be another enzyme that is not listed in this group of enzymes that carry out the described reaction, so that enzyme will be considered as an analogue of the enzyme formate dehydrogenase. Examples of enzymes that can carry out the conversion reaction of formate to $CO_2$ are described in Table 11. The enzymes described in Table 11 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 11

Examples of the enzyme formate dehydrogenase which can be used to transform formate to $CO_2$.

| Name of the gene | Organism |
| --- | --- |
| formate dehydrogenase FDHB | *Wolinella succinogenes* |
| formate dehydrogenase Suden_1824 | *Sulfurimonas denitrificans* |
| formate dehydrogenase Sulku_0269 | *Sulfuricurvum kujiense* |
| formate dehydrogenase sfra | *Geobacter sulfurreducens* PCA |
| formate dehydrogenase sfrB | *Geobacter sulfurreducens* PCA |
| formate dehydrogenase | *Burkholderia stabilis* 15516 |
| formate dehydrogenase sfrB | *Pelobacter carbinolicus* |
| formate dehydrogenase Dbac_0167 | *Desulfomicrobium baculatum* |

The term "acetolactate synthase" (EC 2.2.1.6) refers to a polypeptide having catalytic activity, where this catalytic activity is to transform a compound of pyruvate into 2-acetolactate. However, there may be another enzyme that is not listed in this group of enzymes that carry out the described reaction, so that enzyme will be considered as an analogue of acetolactate synthase. Examples of enzymes that can carry out the conversion reaction of pyruvate to 2-acetolactate are described in Table 12. The enzymes described in Table 12 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 12

Examples of acetolactate synthase which can be used to transform pyruvate to 2-acetolactate.

| Name of the gene | Organism |
| --- | --- |
| Acetolactate synthase ilvN I | Escherichia coli str. K-12 substr. W3110 |
| Acetolactate synthase ilvI III | Escherichia coli str. K-12 substr. W3110 |
| Acetolactate synthase ilvB I, | Mycobacterium tuberculosis H37Rv |
| Acetolactate synthase ilvB | Bacillus subtilis subsp. subtilis str. 168 |
| Acetolactate synthase ILV2 | Saccharomyces cerevisiae S288c chromosome XIII |
| Acetolactate synthase iLV6 | Saccharomyces cerevisiae chromosome III S288c |
| Acetolactate synthase ilvH 3 | Methanococcus aeolicus Nankai-3 |
| Acetolactate synthase CSR1 | Arabidopsis chromosome 3 |

The term "ketoacid reductoisomerase" (EC 1.1.1.86) refers to a polypeptide having catalytic activity, where this catalytic activity is to transform a compound of acetolactate into 2,3-dihydroxyvalerate. However, there may be another enzyme that is not listed in this group of enzymes that carry out the described reaction, so that enzyme will be considered as an analogue of ketoacid reductoisomerase. Examples of enzymes that can carry out the conversion reaction of 2-acetolactate to 2,3-dihydroxyvalerate are described in Table 13. The enzymes described in Table 13 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 13

Examples of ketoacid reductoisomerase which can be used to transform 2-acetolactate to 2,3-dihydroxyvalerate.

| Name of the gene | Organism |
| --- | --- |
| Keto acid reductoisomerase ilvC | Escherichia coli str. K-12 substr. MG1655 |
| Keto acid reductoisomerase ilvC | Escherichia coli str. K-12 substr. W3110 |
| Keto acid reductoisomerase ilvC | Corynebacterium glutamicum ATCC 13032 |
| Keto acid reductoisomerase ilvC | Corynebacterium glutamicum K051 |
| Keto acid reductoisomerase ilvC | Salmonella enterica subsp. serovar Typhimurium str. LT2 |
| Keto acid reductoisomerase ilv5 | Saccharomyces cerevisiae chromosome XII S288c |
| Keto acid reductoisomerase ilvC | Campylobacter jejuni RM1221 |

TABLE 13-continued

Examples of ketoacid reductoisomerase which can be used to transform 2-acetolactate to 2,3-dihydroxyvalerate.

| Name of the gene | Organism |
| --- | --- |
| Keto acid reductoisomerase ilvC | Methylococcus capsulatus str. Bath |
| Keto acid reductoisomerase ilvC | Shewanella oneidensis MR-1 |
| Keto acid reductoisomerase ilvC | Dehalococcoides ethenogenes 195 |
| Keto acid reductoisomerase ilvC | Carboxydothermus hydrogeneoformans Z-2901 |
| Keto acid reductoisomerase ilvC | Listeria monocytogenes serotype 4b str. F2365 |
| Keto acid reductoisomerase ilvC | Geobacter sulfurreducens PCA |
| Keto acid reductoisomerase ilvC | Streptomyces avermitilis MA-4680 |
| Keto acid reductoisomerase ilvC | Pseudomonas aeruginosa PAO1 |

The term "dihydroxyacid dehydratase" (EC 4.2.1.9) refers to a polypeptide having catalytic activity, where this catalytic activity is to transform a compound of 2,3-dihydroxyvalerate into ketoisovalerate. However, there may be another enzyme that is not listed in this group of enzymes that carryout the described reaction, so that enzyme will be considered as an analogue of dihydroxyacid dehydratase. Examples of enzymes that can carry out the conversion reaction of 2,3-dihydroxyvalerate to ketoisovalerate are described in Table 14. The enzymes described in Table 14 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 14

Examples of dihydroxyacid dehydratase which can be used to transform 2,3-dihydroxyvalerate to ketoisovalerate.

| Name of the gene | Organism |
| --- | --- |
| Dihydroxy acid dehydratase ILV3 | Saccharomyces cerevisiae S288c |
| Dihydroxy acid dehydratase IlvD | Shewanella oneidensis MR-1 |
| Dihydroxy acid dehydratase ilvD | Ruegeria pomeroyi DSS-3 |
| Dihydroxy acid dehydratase ilvD | Escherichia coli O157: H7 str. EDL933 |
| Dihydroxy acid dehydratase ilvD | Escherichia coli UTI89 |
| Dihydroxy acid dehydratase ilvD | Escherichia coli CFT073 |
| Dihydroxy acid dehydratase ilvD | Escherichia coli BW2952 |
| Dihydroxy acid dehydratase ilvD | Campylobacter jejuni RM1221 |
| Dihydroxy acid dehydratase ilvD | Dehalococcoides ethenogenes 195 |
| Dihydroxy acid dehydratase ilvD | Methylococcus capsulatus str. Bath |
| Dihydroxy acid dehydratase ilvD | Pseudomonas syringae pv. tomato str. DC3000 |
| Dihydroxy acid dehydratase ilvD | Geobacter sulfurreducens PCA |
| Dihydroxy acid dehydratase ilvD | Listeria monocytogenes serotype 4b str. F2365 |
| Dihydroxy acid dehydratase ilvD | Staphylococcus aureus subsp. aureus N315 |

TABLE 14-continued

Examples of dihydroxyacid dehydratase which can be
used to transform 2,3-dihydroxyvalerate to ketoisovalerate.

| Name of the gene | Organism |
| --- | --- |
| Dihydroxy acid dehydratase ilvD | *Yersinia pestis* Nepal516 |

The term "2-oxoisovalerate dehydrogenase" (EC 1.2.1.25), "3-methyl-2-oxobutanate dehydrogenase" or "ketoacid-dehydrogenase" (EC 1.2.4.4) refers to a polypeptide having catalytic activity, where this catalytic activity is to transform a compound of ketoisovalerate into isobutyryl-CoA, using a molecule of NAD(P)$^+$. However, there may be another enzyme that is not listed in this group of enzymes that carry out the described reaction, so that enzyme will be considered as an analogue of 2-oxoisovalerate dehydrogenase. Examples of enzymes that can carry out the conversion reaction of ketoisovalerate to isobutyryl-CoA are described in Table 15. The enzymes described in Table 15 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 15

Examples of 2-oxoisovalerate dehydrogenase which can
be used to transform ketoisovalerate to isobutyryl-CoA.

| Name of the gene | Organism |
| --- | --- |
| 2-oxoisovalerate dehydrogenase BCKDHA | *Homo sapiens* |
| 2-oxoisovalerate dehydrogenase BCKDHB | *Pan troglodytes* |
| 2-oxoisovalerate dehydrogenase BCDH | *Streptomyces coelicolor* |
| 2-oxoisovalerate dehydrogenase | *Thermoplasma acidophilum* |
| 2-oxoisovalerate dehydrogenase | *Oncorhynchus mykiss* |
| 2-oxoisovalerate dehydrogenase BCKDHA | *Gorilla gorilla gorilla* |
| 2-oxoisovalerate dehydrogenase BCKDHA | golden snub-nosed monkey |

The terms "isobutyryl-CoA mutase" and "isobutyryl-Coenzyme A mutase" (EC 5.4.99.13), refers to a polypeptide having catalytic activity, where this catalytic activity is to transform a compound of isobutyryl-CoA into butyryl-CoA. However, there may be another enzyme that is not listed in this group of enzymes that carry out the described reaction, so that enzyme will be considered as an analogue of isobutyryl-CoA mutase. Examples of enzymes that can carry out the conversion reaction of isobutyryl-CoA to butyryl-CoA are described in Table 16. The enzymes described in Table 16 are shown for reference only, since there are many databases where one can find more examples of these enzymes, such as the GeneBank (http://www.ncbi.nlm.nih.gov), the Kyoto Encyclopedia of Genes and Genomes (http://www.kegg.jp), the Braunschweig Enzyme Database (http://www.brenda-enzymes.org), etc.

TABLE 16

Examples of isobutyryl-CoA mutase which can be
used to transform isobutyryl-CoA to butyryl-CoA.

| Name of the gene | Organism |
| --- | --- |
| isobutyryl-CoA mutase icma | *Streptomyces coelicolor* A3 (2) |
| isobutyryl-CoA mutase | *Streptomyces cinnamonensis* |

The present invention refers to a method wherein a multi-enzyme system produces butanol starting from lactate sequentially coupled with a regeneration system of NAD (P)+/NAD (P) H and/or regeneration of acetyl-CoA/CoA (FIG. 1). This transformation can be performed in a container or reactor where the whole process can be carried out continuously, semicontinuously or in batch.

Furthermore, the present invention overcomes the deficiencies of the prior art by providing polypeptides that, with an experimental performance equal or lower than the theoretical yield, transform lactate sequentially to butanol.

Furthermore, the present invention can use smaller amounts than stoichiometrically required of NAD (P)+, NAD (P) H and CoA to perform the process described above, because the method of the present invention allows the regeneration of NAD(P)$^+$/NAD(P)H and/or the regeneration of acetyl-CoA/CoA in three different ways: a) during the conversion of lactate to pyruvate, of pyruvate to acetyl-CoA, acetoacetyl-CoA to (S)-3-hydroxybutanoyl-CoA, of crotonyl-CoA to butanoyl-CoA, of butanoyl-CoA to butanal and butanal to butanol; b) during the conversion of lactate to pyruvate, formate to $CO_2$, of acetoacetyl-CoA to (S)-3-hydroxybutanoyl-CoA, of crotonyl-CoA to butanoyl-CoA, of butanoyl-CoA to butanal and of butanal to butanol; c) during the conversion of lactate to pyruvate, of acetolactate to hydroxyvalerate, of ketoisovalerate to isobutyryl-CoA, of butanoyl-CoA to butanal and of butanal to butanol.

In turn, the method of the present invention may employ unitary operations recirculating to system NAD (P)+ and/or NAD (P) H and/or CoA, allowing lower amounts than those established by the stoichiometry amounts to be transformed to larger amounts of lactate to butanol.

The present invention may employ the enzymes lactate dehydrogenase (EC 1.1.1.27 and/or EC 1.1.1.28), pyruvate dehydrogenase (EC 1.2.4.1, EC 2.3.1.12, EC 1.8.1.4 and EC 1.2.1.51), acetoacetyl-CoA thiolase (EC 2.3.1.9), hydroxybutyryl-CoA dehydrogenase (EC 1.1.1.35 and or EC 1.1.1.157), (S)-3-hydroxybutanoyl-CoA hydro-lyase (EC 4.2.1.55) and or enoyl-CoA hydratase (EC 4.2.1.17), trans-2-enoyl-CoA reductases (EC 1.3.1.44) and or butyryl-CoA dehydrogenase (EC 1.3.1.86 and or EC 1.3.8.1), butanal dehydrogenase (EC 1.2.1.57) and or acetaldehyde dehydrogenase (EC 1.2.1.10) and alcohol dehydrogenase (EC 1.1.1.1 and/or EC 1.1.1.2) and or its analogs to transform lactate into butanol, wherein the amount of NAD (P)+ added to the system may be less than the amount set by the stoichiometry for the conversion of lactate into butanol, and wherein the experimental yield obtained in the transformation of lactate into butanol is equal or lower than theoretical material usage (0.411 grams of butanol per gram of lactate).

At the same time, the present invention may also employ the enzymes lactate dehydrogenase (EC 1.1.1.27 and or EC 1.1.1.28), pyruvate formate-lyase (EC 2.3.1.54), formate dehydrogenase (EC 1.2.1.43), acetoacetyl-CoA thiolase (EC 2.3.1.9), hydroxybutyryl-CoA dehydrogenase (EC 1.1.1.35 and/or EC 1.1.1.157), (S)-3-hydroxybutanoyl-CoA hydro-lyase (EC 4.2.1.55) and/or enoyl-CoA hydratase (EC 4.2.1.17), trans-2-enoyl-CoA reductase (EC 1.3.1.44) and/or butyryl-CoA dehydrogenase (EC 1.3.1.86 and/or EC 1.3.8.1), butanal dehydrogenase (EC 1.2.1.57) and/or acetaldehyde dehydrogenase (EC 1.2.1.10) and alcohol dehydrogenase (EC 1.1.1.1 and/or EC 1.1.1.2) and/or its analogs to transform lactate into butanol, wherein the amount of NAD (P)+ added to the system may be less than the amount set by the stoichiometry for conversion of lactate into butanol, and wherein the experimental yield obtained in the transformation of lactate to butanol is equal or lower than theoretical material usage (0.411 grams of butanol per gram of lactate).

Also, the present invention may employ the enzymes lactate dehydrogenase (EC 1.1.1.27 and/or EC 1.1.1.28), acetolactate synthase (EC 2.2.1.6), ketoacid reductoisomerase (EC 1.1.1.86), dihydroxyacid dehydratase (EC 4.2.1.9), 2-oxoisovalerato dehydrogenase (EC 1.2.1.25) and/or ketolacid dehydrogenase (EC 1.2.4.4), isobutyryl-Coenzyme A mutase (EC 5.4.99.13), butanal dehydrogenase (EC 1.2.1.57) and/or acetaldehyde dehydrogenase (EC 1.2.1.10) and alcohol dehydrogenase (EC 1.1.1.1 and/or EC 1.1.1.2) and/or its analogs to transform lactate into butanol, wherein the quantity of NAD (P)+ added to the system may be less than the amount set by the stoichiometry for the conversion of lactate into butanol, and wherein the experimental yield obtained in the transformation of lactate to butanol is equal or lower than theoretical material usage (0.411 gr of butanol for a gram of lactate)

In another embodiment of the present invention, there is provided a method for the production of butanol from lactate, engaged with a system of regeneration of NAD(P)$^+$/NAD(P)H and the regeneration of acetyl-CoA/CoA, wherein the operation mode is continued using free enzymes. The enzyme mixture may be any of those described above. This method comprises different stages which are described below:

I. A mixture is prepared continuously starting from water, lactate, the enzyme mixture, NAD(P)$^+$/NAD(P)H, CoA and the cofactors and coenzymes that uses the enzymes to perform catalysis. The cofactors and coenzymes depend on the nature of each enzyme. In Table 17 are shown some of the cofactors and coenzymes used by the different enzymes in the present invention. The cofactors and coenzymes described in Table 17 are examples, this does not exempt other cofactors or coenzymes to be used by enzymes to perform catalysis.

II. The flow obtained from stage I is passed continuously through a reactor that stably maintains the conditions of reaction of pH between 4 and 10, preferably between 6 and 8 and at a temperature between 15° C. and 40° C., preferably between 25° C. and 37° C. When this current enters the reactor, it carries out the production of butanol from lactate with a conversion efficiency equal to or less than 100%.

III. At the outflow of the reactor enriched with butanol and depleted of lactate, one can separate the cofactors, the coenzymes and enzymes by passing it through a separation system. The enzymes, coenzymes and cofactors form a concentrated stream which can be recycled to step I or else to the reactor.

IV. At the outflow of the reactor enriched with butanol and depleted of lactate, one can separate the cofactors, the coenzymes and enzymes by passing it through a separation system. The separation system can be: a membrane system (reverse osmosis, nanofiltration, ultrafiltration, etc.), distillation, evaporation or any other system that allows the separation of molecules either by size or by any of its physiochemical properties.

TABLE 17

Coenzymes and cofactors used by the enzymes to form the enzyme mixture

| Enzyme name | Source | cofactors | coenzymes |
|---|---|---|---|
| Pyruvate dehydrogenase | Escherichia coli | MG $^{2+}$ | THPP, FAD |
| Pyruvate dehydrogenase | Saccharomyces cerevisiae | | THPP, FAD |
| Pyruvate dehydrogenase | Azotobacter vinelandii | Mg $^{2+}$ | THPP |
| Pyruvate dehydrogenase | Salmonella enterica subsp enterica serovar Typhimurium | | THPP |
| Pyruvate dehydrogenase | Enterobacter cloacae | | THPP |
| 3-hydroxyacyl-CoA dehydrogenase | Clostridium kluyvery | Se $^{2+}$ | |
| Enoyl CoA hydratase- | Clostridium aminobutyricum | Fe $^{2+}$ | FAD |
| Butyryl-CoA Dehydrogenase | Clostridium difficile | | Ferredoxin, FAD |
| Butyryl-CoA Dehydrogenase | Pseudomonas putida | | FAD |
| Butyryl-CoA Dehydrogenase | Clostridium kluyveri | Fe $^{2+}$ | FAD |
| acetaldehyde dehydrogenase | Escherichia coli | Fe $^{2+}$ Fe $^{2+}$ | CoA |
| acetaldehyde dehydrogenase | Acinetobacter sp | Mn $^{2+}$ | |
| Alcohol dehydrogenase | Oenococcus oeni | Mg $^{2+,}$ Na $^{+,}$ Ni $^{2+}$ | |
| Alcohol dehydrogenase | Saccharomyces cerevisiae | Co $^{2+,}$ Zn $^{2+,}$ | |
| Alcohol dehydrogenase | Geobacillus thermodenitrificans | Fe $^{2+,}$ Na $^{2+,}$ | |
| Alcohol dehydrogenase | Acetobacter pasteurianus SKU1108 | Zn $^{2+,}$ NAD(P) +, | |
| Alcohol dehydrogenase | Natronomonas pharaonic | K $^{+,}$ Na $^{+}$ | |
| Alcohol dehydrogenase | Emericella nidulans | Zn $^{2+}$ | |
| Alcohol dehydrogenase | Flavobacterium frigidimaris KUC-1 | Zn $^{2+}$ | |
| Alcohol dehydrogenase | Desulfovibrio gigas | Zn $^{2+}$ | |
| Alcohol dehydrogenase | Saccharomyces cerevisiae | Zn $^{2+}$ | |

In another embodiment of the present invention, another method is provided for the production of butanol out of lactate, coupled with a system of regeneration of NAD(P)$^+$/NAD(P)H and the regeneration of acetyl-CoA/CoA, wherein the mode of operation is continued using immobilized enzymes. The mixture of immobilized enzymes can be any of those described above. The immobilization of enzymes on the support can be carried out by any method that is appropriate. Table 18 shows some of the supports used to immobilize enzymes. The supports described in Table 18 are examples of some supports, this does not exclude other materials that are suitable for the immobilization of enzymes and which are not in Table 18. This method comprises different stages which are described below:

I. A mixture of the enzymes are immobilized on a support. The support can also be multiple supports of the same type with different numbers of enzymes, or may be supports of different types, sizes or chemical compositions and each support containing one or more enzymes, such that in the reactor are all enzymes either on the same support or on different supports. Coenzymes and cofactors may also be present on the support. Once the enzymes are immobilized, these immobilized enzymes and their supports will be added to the reactor.

II. A mixture is prepared continuously from water, lactate and NAD(P)⁺/NAD(P)H. Cofactors and coenzymes employed by each enzyme to perform catalysis depend on the nature of each enzyme. Some of the cofactors and coenzymes employed by the different enzymes used in the present invention are shown in Table 17. Cofactors and coenzymes described in Table 17 are examples, this does not exclude other cofactors or coenzymes that could be used by enzymes to perform catalysis.

III. The stream exiting stage II, is passed continuously through the reactor containing the immobilized enzymes, so that this flow is continuously in contact with said enzymes, stably maintaining the conditions of reaction at pH between 4 and 10, preferably between 6 and 8 and at a temperature between 15° C. and 40° C., preferably between 25° C. and 37° C. When this stream is contacted with enzymes, the production of butanol from lactate is carried out with a conversion efficiency equal to or less than 100%. Preferably the support is maintained within the reactor, although the output of the reactor support does not imply that this support can not be recirculated to the reactor.

IV. The outflow of stage III, enriched and depleted butanol lactate, can go through a separation system, where the co-enzymes and cofactors butanol and water are separated. Coenzymes and cofactors form a concentrated stream which can be recycled to stage II, or to the enzyme reactor.

V. Regarding the outflow of stage III, whether or not coenzymes and cofactors have been separated, one can separate the fraction of butanol in another separation system. This system generates two streams, a butanol water stream and another stream.

Separation systems mentioned in stages IV and V can be: membrane system (reverse osmosis, nanofiltration, ultrafiltration, etc.), distillation, evaporation or any other system which allows the separation of molecules, either by their size or for some of its physicochemical properties.

TABLE 18

Supports used to immobilize enzymes.

| Support | Enzyme | Reference |
|---|---|---|
| Calcium Alginate | lipase | Wonâ on 2005 |
| Silica Gel | peroxidase | Lia on 1996 |
| zeolite | glucose oxidase | Liu on 1997 |
| Perlite | cholesterol oxidase | Torabi on 2007 |

EXAMPLES

The following examples are intended to clarify the present invention. It should be understood that the following examples do not constitute a limitation on the scope of the present invention. From the description of the invention and the following examples, a person skilled in the field of the invention can make some modifications which anyway remain within the scope protected by the present invention.

Example 1. Quantification of Enzyme Activity

To determine the enzymatic activity of different enzymes, first the different genes of the enzymes were cloned into commercial expression vectors, such as the DUET (Merck, USA) series, following the protocols described in Green and Sambrook, 2010. Subsequently enzymes were purified according to protocols described in Sambrook and Green, 2010.

Enzyme assays and results are described below:

a) Lactate Dehydrogenase (EC 1.1.1.27 and/or EC 1.1.1.28)

Lactate dehydrogenase can transform lactate to pyruvate using NAD $(P)^{+,}$ so the test was conducted by varying the initial concentrations of lactate, NAD $(P)^{+,}$ pH and temperature following the protocols described in the literature (Cetinel et al., 2013). Four enzymes of various microorganisms were used (*Escherichia coli* APEC O1, *Escherichia coli* PMV-1, *Lactobacillus lactis* subsp. lactis IL1403 and *Streptococcus pneumoniae* AP200). The conditions tested are shown in Table 19.

TABLE 19

Reaction conditions tested for lactate dehydrogenase enzyme (EC 1.1.1.27 and/or EC 1.1.1.28).

| Variable | test conditions |
|---|---|
| pH | 5, 7 and 10 |
| Temperature (° C.) | 5, 25, 35 and 55 |
| Lactate (g/L) | 1, 50, 100, 200, 300 |
| NAD(P)⁺ (g/L) | 1, 5, and 10 |

In all tests performed conversion of lactate to pyruvate production was observed as NAD (P) H after 1 hour.

) Pyruvate Dehydrogenase Complex (EC 1.2.1.51, EC 1.2.4.1, EC 2.3.1.12 and EC 1.8.1.4)

The pyruvate dehydrogenase complex transforms pyruvate into acetyl-CoA, using a molecule of NAD $(P)^{+,}$ so the test was conducted by varying the initial concentrations of pyruvate, NAD $(P)^{+,}$ CoA, pH and temperature following the protocols described in the literature (Nemeria et al., 2001). Three enzymes from different microorganisms were used (*Escherichia coli* K-12 MG1655. *Corynebacterium* sp. ATCC 6931 and *Lactobacillus reuteri*). The conditions tested are shown in Table 20.

TABLE 20

Reaction conditions tested for pyruvate dehydrogenase complex (EC 1.2.4.1, EC 2.3.1.12, EC 1.8.1.4 and EC 1.2.1.51).

| Variable | test conditions |
|---|---|
| pH | 5, 7 and 10 |
| Temperature (° C.) | 5, 25, and 55 |
| Pyruvate (g/L) | 1, 25, 50 and 100 |
| NAD(P)⁺ (g/L) | 1, 5, and 10 |
| CoA | 1, 5, and 10 |

In all trials consumption both NAD (P)⁺ was observed as pyruvate after one hour reaction.

c) Acetyl-CoA Thiolase (2.3.1.9)

Acetyl-CoA thiolase enzyme converts two molecules of acetyl-CoA in a molecule of acetoacetyl-CoA, so the test was conducted by varying the initial concentrations of acetyl-CoA, pH and temperature following the protocols described in the literature (Huth et al., 1975). Three enzymes from different microorganisms were used (.: H 18 042 *Xanthomonas campestris* pv *campestris* ATCC 33913, *Shigella sonnei* and *Escherichia coli* O44 Ss046). The conditions tested are shown in Table 21.

TABLE 21

Reaction conditions tested for enzyme acetyl-CoA thiolase (2.3.1.9).

| Variable | test conditions |
|---|---|
| pH | 5, 7, and 10 |
| Temperature (° C.) | 5, 25 and 55 |
| Acetyl-CoA (g/L) | 1, 25 and 75 |

In all trials consumption of acetyl CoA it was observed after one hour reaction.

d) 3-hydroxybutyryl-CoA Dehydrogenase (EC 1.1.1.35 and/or 1.1.1.157)

3-hydroxybutyryl-CoA dehydrogenase converts acetoacetyl-CoA to 3-hydroxybutyryl-CoA, using a molecule of NAD (P) H, so the test was conducted by varying the initial concentrations of acetoacetyl-CoA, NAD (P) H, pH and temperature following the protocols described in the literature (Madan et al., 1973). Three enzymes from different microorganisms were used (: H2 12009, *Xanthomonas albilineans, Escherichia coli* O103 *Aspergillus niger*). The conditions tested are shown in Table 22.

TABLE 22

Reaction conditions tested for hydroxybutyryl-3-CoA dehydrogenase (EC 1.1.1.35).

| Variable | test conditions |
|---|---|
| pH | 5, 7 and 10 |
| Temperature (° C.) | 5, 25 and 55 |
| Acetoacetyl-CoA (g/L) | 1, 25 and 50 |
| NADP(H) (g/L) | 1, 5, and 10 |

In all trials consumption NAD (P) H after 30 minutes reaction was observed.

e) Enoyl CoA Hydratase (EC 4.2.1.17)

The enoyl-CoA hydratase can transform 3-hydroxybutyryl-CoA to crotonyl-CoA, so the test was conducted by varying the initial concentrations of 3-hydroxybutyryl-CoA, pH and temperature following the protocols described in the literature (Fukui et al., 1998). Three enzymes from different microorganisms were used (*Acinetobacler baumannii*, and *Arabidopsis thaliana Escherichia coli* K-12 MDS42). The conditions tested are shown in Table 23.

TABLE 23

Reaction conditions tested for enzyme enoyl-CoA hydratase (EC 4.2.1.17).

| Variable | test conditions |
|---|---|
| pH | 2, 5, 7, 10 and 12 |
| Temperature (° C.) | 5, 15, 25, 35, 45 and 55 |
| 3-hydroxybutyryl-CoA (g/L) | 1, 25, 50 and 75 |

In all trials consumption hydroxybutyryl-CoA was observed after 30 minutes of reaction.

f) Butyryl-CoA Dehydrogenase (EC 1.3.1.44, 1.3.1.86 and/or 1.3.8.1)

The butyryl-CoA dehydrogenase enzyme converts crotonyl-CoA to butanoyl-CoA using a molecule of NAD (P) H, so the test was conducted by varying the initial concentrations of crotonyl-CoA, NAD (P) H, pH and temperature following the protocols described in the literature (Hu et al., 2013). Three enzymes from different microorganisms were used (*Clostridium acetobutylicum* DSM 1731, *Clostridium perfringenes Streptomyces griseus* and 13). The conditions tested are shown in Table 24.

TABLE 24

Reaction conditions tested for butanoyl-CoA oxidoreductase (EC 1.3.1.44).

| Variable | test conditions |
|---|---|
| pH | 2, 5, 7, 10 and 12 |
| Temperature (° C.) | 5, 15, 25, 35, 45 and 55 |
| Crotonyl-CoA (g/L) | 1, 25, 50 and 75 |
| NAD (P) H (g/L) | 1, 5, and 10 |

In all trials consumption NAD (P) H after 30 minutes reaction was observed.

h) Butyraldehyde Dehydrogenase (EC 1.2.1.57 and/or EC 1.2.1.10)

Dehydrogenase butanal enzyme transforms butanoyl-CoA to butanal using a molecule of NAD (P) H, so the test was conducted by varying the initial concentrations of butanoyl-CoA, NAD (P) H, pH and temperature following the protocols described in the literature (Palosaari and Rogers, 1988). Three enzymes from different microorganisms were used (: *Clostridium acetobutylicum* DSM SE15 H5 1731, *Escherichia coli* and *Salmonella enterica* O150). The conditions tested are shown in Table 25.

TABLE 25

Reaction conditions tested for butanal dehydrogenase enzyme (EC 1.2.1.57).

| Variable | test conditions |
|---|---|
| pH | 5, 7 and 10 |
| Temperature (° C.) | 5, 25 and 55 |
| Butanoyl-CoA (g/L) | 1, 50 and 75 |
| NAD (P) H (g/L) | 1, 5, and 10 |

In all trials consumption NAD (P) H after 30 minutes reaction was observed.

i) Alcohol Dehydrogenase (EC 1.1.1.1 and/or EC 1.1.1.2)

Alcohol dehydrogenase can transform isobutyraldehyde into isobutanol using NAD (P) H, so the test was conducted by varying the initial concentrations of isobutyraldehyde, NAD (P) H, pH and temperature following the protocols described in the literature (Atsumi et al., 2010). Three enzymes from different microorganisms were used (*Escherichia coli* K-12 MDS42, *Bacillus cereus* and *Clostridium acetobutylicum* DSM B4264 1731). The conditions tested are shown in Table 26.

TABLE 26

Reaction conditions tested for the enzyme alcohol dehydrogenase (EC 1.1.1.1 and/or EC 1.1.1.2)

| Variable | test conditions |
|---|---|
| pH | 5, 7 and 12 |
| Temperature (° C.) | 5, 35 and 55 |
| Isobutyraldehyde (g/L) | 1, 25 and 75 |
| NAD (P) H (g/L) | 1, 5, and 10 |

In all tests performed both isobutyraldehyde to isobutanol conversion was observed after 15 minutes as reaction consuming NAD (P) H.

j) Pyruvate Formate-Lyase (EC 2.3.1.54)

The enzyme pyruvate formate lyase converts pyruvate to Acetyl-CoA and $CO_2$, so the test was conducted by varying the initial concentrations of pyruvate, pH and temperature following the protocols described in the literature (Takahashi, et al., 1982). Three enzymes from different microorganisms were used (*Lucimarinus ostreococcus, Bathycoccus prasinos* and *Escherichia coli* K-12 MG1655). The conditions tested are shown in Table 27.

TABLE 27

| Reaction conditions tested for enzyme pyruvate formate lyase (EC 2.3.1.54) | |
| --- | --- |
| Variable | test conditions |
| pH | 5, 7 and 10 |
| Temperature (° C.) | 5, 35 and 55 |
| Pyruvate (g/L) | 1, 50 and 100 |

In all tests performed pyruvate consumption was observed after one hour of reaction.

k) Formate Dehydrogenase (EC 1.2.1.43)

The enzyme formate dehydrogenase transforms the formate into $CO_2$ using a molecule of NAD $(P)^+$, so the test was conducted by varying the initial concentrations of formate, NAD $(P)^+$, pH and temperature following the protocols described in literature (Hatrongjit and Packdibamrung, 2010). Three enzymes from different microorganisms were used (*Wolinella succinogenes, Sulfuricurvum kujiense* and *Geobacter sulfurreducens* PCA). The conditions tested are shown in Table 28.

TABLE 28

| Reaction conditions tested for the enzyme formate dehydrogenase (EC 1.2.1.43). | |
| --- | --- |
| Variable | test conditions |
| pH | 5, 7 and 10 |
| Temperature (° C.) | 5, 35 and 55 |
| Pyruvate (g/L) | 1, 50 and 100 |
| NAD $(P)^+$ (g/L) | 1, 5, and 10 |

In all tests conducted formate consumption and NAD $(P)^+$ was observed after 2 hours of reaction.

l) Acetolactate Synthase (EC 2.2.1.6)

Acetolactate synthase converts pyruvate into 2-acetolactate, so the test was conducted by varying the initial concentrations of pyruvate, pH and temperature following the protocols described in the literature (Holtzclaw and Chapman, 1975; Barak et al, 1987; Atsumi et to the. 2009). Three enzymes from different microorganisms were used (*Escherichia coli* were used K-12 MG1655, *Bacillus subtilis* subsp. *subtilis* str. 168 and *Saccharomyces cerevisiae*, S288c). The conditions tested are shown in Table 29.

TABLE 29

| Reaction conditions tested for the enzyme acetolactate synthase (EC 2.2.1.6). | |
| --- | --- |
| Variable | test conditions |
| pH | 5, 7, 10 |
| Temperature (° C.) | 5, 35 and 55 |
| Pyruvate (g/L) | 1, 50 and 100 |

In all tests performed pyruvate consumption was observed after 20 minutes of reaction.

m) Keto Acid Reductoisomerase (EC 1.1.1.86) and Dihydroxy Acid Dehydratase (EC 4.2.1.9)

On one hand, the keto acid reductoisomerase 2-acetolactate transforms 2,3-dihydroxyvalerate while dihydroxyacid dehydratase transforms hydroxyvalerate into ketoisovalerate. Because the 2-acetolactate is not a commercial compound as 2,3-dihydroxyvalerate is an unstable compound, the determination of the activity of these two enzymes was measured indirectly by coupling a test acetolactate synthase with keto acid reductoisomerase and dihydroxy acid dehydratase. This was done by varying the initial concentrations of pyruvate, NAD (P) H, pH and temperature using as a basis the protocols described in the literature (Flint et al., 1993; Bastian et al, 2011; Li et al, 2011). Reductoisomerase combination of two enzymes and two dihydroxy keto acid dehydratase enzymes from different microorganisms were used (*Escherichia coli* K-12 MG1655, *Escherichia coli* UTI89 *Staphylococcus aureus, Corynebacterium glutamicum* ATCC 13032). The conditions tested are shown in Table 30.

TABLE 30

| Reaction conditions tested for ketoacid reductoisomerase (EC 1.1.1.86) and dihydroxy acid dehydratase (EC 4.2.1.9). | |
| --- | --- |
| Variable | test conditions |
| pH | 5, 7 and 10 |
| Temperature (° C.) | 5, 35 and 55 |
| Pyruvate (g/L) | 1, 10 and 25 |
| NAD (P) H (g/L) | 1, 5, and 10 |

In all trials consumption pyruvate and NAD (P) H was observed after 2 hours of reaction.

n) 2-oxoisovalerate Dehydrogenase (EC 1.2.1.25 and/or EC 1.2.4.4)

The enzyme 2-oxoisovalerate dehydrogenase transforms ketoisovalerate to isobutyryl-CoA, using a molecule of NAD $(P)^+$, so the test was conducted by varying the initial concentrations of ketoisovalerate, NAD $(P)^+$, pH and temperature following the protocols described in the literature (Hakozaki et al., 2002). Three enzymes from different organisms were used (*Streptomyces coelicolor* and *Thermoplasma acidophilum* and *Oncorhynchus mykiss*). The test conditions are shown in Table 31.

TABLE 31

| Reaction conditions tested for the enzyme 2-oxoisovalerato dehydrogenase (EC 1.2.1.25 and/or EC 1.2.4.4). | |
| --- | --- |
| Variable | test conditions |
| pH | 5, 7, 10 |
| Temperature (° C.) | 5, 35 and 55 |
| ketoisovalerate (g/L) | 1, 50 and 100 |
| NAD (P) H (g/L) | 1, 5, and 10 |

In all tests we performed ketoisovalerate consumption and NAD $(P)^+$ was observed after one hour of reaction.

o) Isobutyryl-CoA Mutase (EC 5.4.99.13)

The isobutyryl-CoA mutase transforms isobutyryl-CoA to butyryl-CoA, so the test was conducted by varying the initial concentrations of isobutyryl-CoA, pH and temperature following the protocols described in the literature (Ratnatilleke et al., 1999). 2 enzymes from different organisms were used (*Streptomyces coelicolor* A3 (2) and *Streptomyces cinnamonensis*). The conditions tested are shown in Table 32.

TABLE 32

Reaction conditions tested for isobutyryl-CoA mutase (EC 5.4.99.13).

| Variable | test conditions |
| --- | --- |
| pH | 5, 7, 10 |
| Temperature (° C.) | 5, 35 and 55 |
| isobutyryl-CoA | 1, 15 and 30 |

In all trials consumption isobutyryl-CoA was observed after 45 minutes of reaction.

Example 2. Enzymatic production of butanol from lactate, coupled with a regeneration system of NAD (P)$^+$/NAD (P) H and/or regeneration of acetyl-CoA/CoA in a batch process.

This example is intended to demonstrate the concept of regeneration of NAD (P)$^+$/NAD (P) H and/or regeneration of acetyl-CoA/CoA in a batch process when enzyme lactate dehydrogenase (EC 1.1.1.27 and/or EC 1.1.1.28), pyruvate dehydrogenase (EC 1.2.1.51, EC 1.2.4.1, EC 2.3.1.12 and/or EC 1.8.1.4), acetoacetyl-CoA thiolase (EC 2.3.1.9), 3-hydroxybutyryl-CoA dehydrogenase (EC 1.1.1.35 and/or EC 1.1.1.157), enoyl-CoA hydratase (EC 4.1.1.55 and/or EC 4.2.1.17), butyryl-CoA dehydrogenase (EC 1.3.1.44, EC 1.3.1.86 and/or 1.3.8.1), butanal dehydrogenase (EC 1.2.1.57 and/or EC 1.2.1.10), alcohol dehydrogenase (EC 1.1.1.1 and/or EC 1.1.1.2), or its analogs, according to the following reactions:

Conversion reaction of lactate to pyruvate. In this reaction two molecules of NAD (P) H are formed from two molecules of NAD (P)$^+$ with the transformation of two molecules of lactate to two pyruvate molecules, this reaction can be performed by the enzyme lactate dehydrogenase (EC 1.1.1.27 and/or EC 1.1.1.28) or any of its analogs:

$$2C_3H_6O_3+2NAD(P)^+==>2C_3H_4O_3+2NAD(P)H+2H^+ \qquad (1)$$

Conversion reaction of pyruvate to acetyl-CoA. In this reaction two molecules of NAD (P) H are formed from two molecules of NAD (P)$^+$ with the transformation of two molecules of pyruvate into two molecules of acetyl-CoA, this reaction can be carried out using pyruvate complex dehydrogenase (EC 1.2.1.51, EC 1.2.4.1, EC 1.8.1.4 and EC 2,3,1,12) or its analogs:

$$2C_3H_4O_3+2NAD(P)^++2CoA=>2C_{23}H_{38}N_7O_{17}P_3S+ \\ 2NAD(P)H+2H^++2CO_2 \qquad (2)$$

Transformation reaction of acetyl-CoA into acetoacetyl-CoA. In this reaction two molecules of acetyl-CoA are converted into a molecule of acetoacetyl-CoA, this reaction can be carried out by acetoacetyl-CoA thiolase enzyme (EC 2.3.1.9) or its analogues:

$$2C_{23}H_{38}N_7O_{17}P_3S==>C_{25}H_{40}N_7O_{18}P_3S+CoA \qquad (3)$$

Transformation reaction of acetoacetyl-CoA to 3-hydroxybutyryl-in CoA. In this reaction one molecule of NAD (P)+ is formed from one molecule of NAD (P) H, with the transformation of a molecule of acetoacetyl-CoA in a molecule of 3-hydroxybutyryl-CoA, this reaction can be performed using hydroxybutyryl-3-CoA dehydrogenase (EC 1.1.1.35 and/or EC 1.1.1.157) or its analogs:

$$C_{25}H_{40}N_7O_{18}P_3S+NAD(P)H^+H+==> \\ C_{25}H_{42}N_7O_{18}P_3S+NAD(P)^+ \qquad (4)$$

Transformation reaction of 3-hydroxybutyryl-CoA to crotonyl-CoA. In this reaction one molecule of 3-hydroxybutyryl-CoA becomes a molecule of crotonyl-CoA and water, this reaction can be carried out using enoyl-CoA hydratase enzyme (EC 4.1.1.55 and/or EC 4.2.1.17) or its analogs:

$$C_{25}H_{42}N_7O_{18}P_3S==>C_{25}H_{40}N_7O_{17}P_3S+H_2O \qquad (5)$$

Transformation reaction of crotonyl-CoA to butanoyl-CoA. In this reaction one molecule of NAD (P)$^+$ is formed from one molecule of NAD (P) H, with the transformation of a molecule of crotonyl-CoA in a molecule of butanoyl-CoA, this reaction can be carried out using butyryl-CoA dehydrogenase (EC 1.3.1.44, EC 1.3.1.86 and/or 1.3.8.1) or any of its analogs:

$$C_{25}H_{40}N_7O_{17}P_3S+NAD(P)H+H^+==> \\ C_{25}H_{42}N_7O_{17}P_3S+NAD(P)^+ \qquad (6)$$

Transformation reaction of butanoyl-CoA into butanal. In this reaction molecule of NAD (P)+ is formed from one molecule of NAD (P) H, with the transformation of a molecule butanoyl-CoA in a molecule butanal, this reaction can be carried out using butanal dehydrogenase enzyme (EC 1.2.1.57 and/or EC 1.2.1.10) or any of its analogs:

$$C_{25}H_{42}N_7O_{17}P_3S+NAD(P)H+H^+==>C_4H_8O+NAD \\ (P)^++CoA \qquad (7)$$

Transformation reaction of butanal into butanol. In this reaction one molecule of NAD (P)$^+$ is formed from one molecule of NAD (P) H, with the formation of one molecule of butanol from a molecule butanal, this reaction can be performed using enzyme Alcohol dehydrogenase (EC 1.1.1.1 and/or EC 1.1.1.2):

$$C_4H_8O+NAD(P)H+H^+==>C_4H_{10}O+NAD(P)^+ \qquad (8)$$

From the above equations, the overall stoichiometric equation of multi-enzymatic system has no loss or gain of NAD (P)$^+$, NAD (P) H, CoA and/or acetyl-CoA, so that the overall reaction results in the use of two molecules of lactate to produce a molecule of butanol, obtaining an efficiency of 100% conversion according to the following reaction:

$$2C_3H_6O_3==>C_4H_{10}O+2CO_2+H_2O \qquad (9)$$

Figure 2:
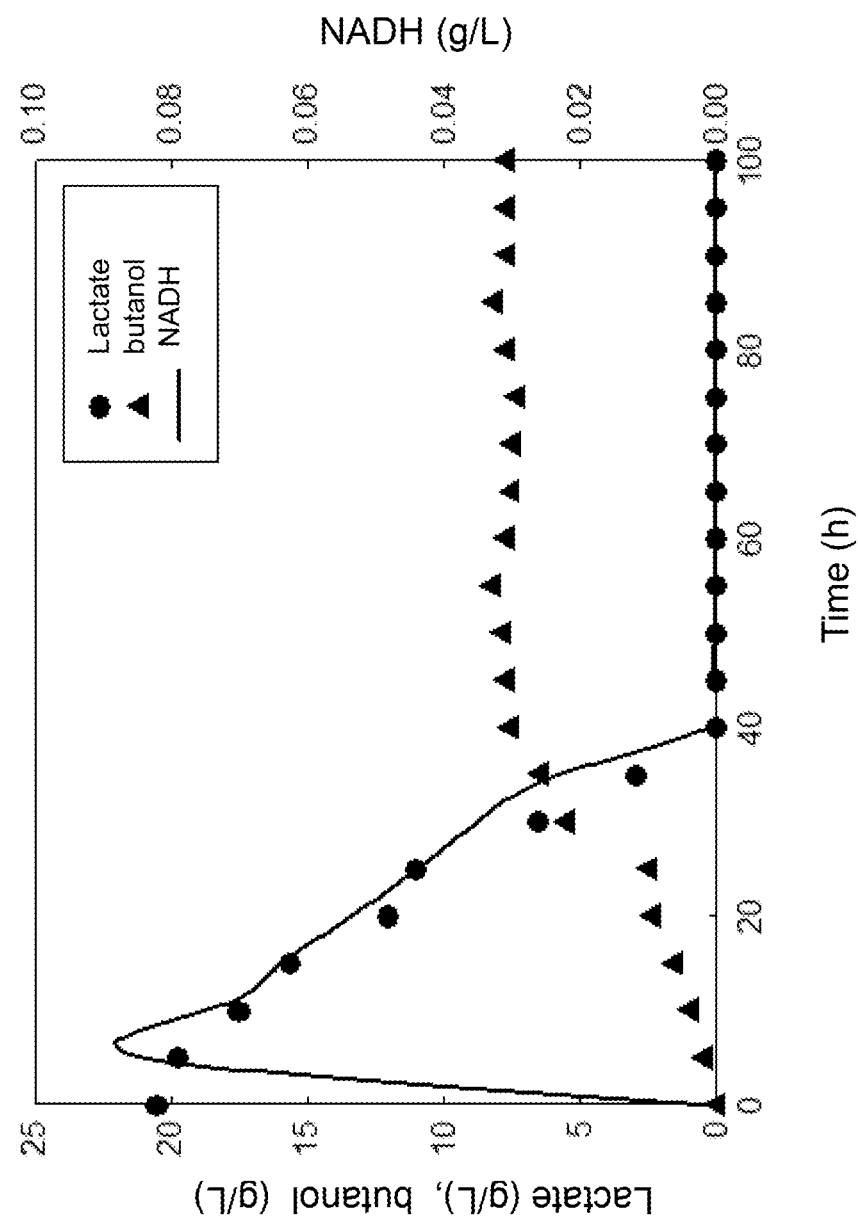
FIG. 2 shows a graph illustrating the behavior of the batch production method of butanol.

To attach the regeneration of NAD (P)$^+$/NAD (P) H and/or regeneration of acetyl-CoA/CoA with the production of butanol from lactate, a batch system was developed for use in different operating conditions (Table 33). The reaction mixture was formulated with the enzyme mixture (Table 34), cofactors and coenzymes (at the concentrations described in the prior art), lactic acid and NAD (P)+. In FIG. 2 the result of one of the conditions made to the batch process is shown. In this particular operating condition a volume of 1 L with an initial concentration of L-lactate 20 g/L and NAD (P)$^+$0.1 g/L was used. The concentration of each of the enzymes in the reaction mixture was adjusted to 1 g/L. Significantly, for the different conditions shown in Tables 33 and 34, similar behaviors were obtained.

In all cases, the reaction was initiated with the addition of lactate. From this point, the reaction medium was continuously sampled to determine the progress of the reaction. The variation in time of NADH and/or NADPH was measured on a Cary-60 spectrophotometer at a wavelength of 340 nm. Lactate and butanol were monitored by HPLC with refractive index detector using a Rezex ROA-organic acids H$^+$ column.

TABLE 33

Reaction conditions for the production of butanol from lactate in batch.

| Reaction Conditions | Value Range |
| --- | --- |
| Trading volume (L) | 1-100 |
| Temperature (° C.) | 20-37 |
| pH | 6-8 |
| Lactate (g/L) | 1-300 |
| NAD (P)$^+$ (g/L) | 0.01-10 |
| CoA (g/L) | 0.01-10 |

TABLE 34

Enzymes used to formulate the enzyme mixture to produce butanol from lactate.

| Enzyme | Concentration in the enzyme mixture (g/L) |
| --- | --- |
| Lactate dehydrogenase (EC 1.1.1.27 and/or EC 1.1.1.28) | 1-10 |
| Pyruvate dehydrogenase (EC 1.2.1.51, EC 1.2.4.1, EC 2.3.1.12 and/or EC 1.8.1.4) | 1-10 |
| Acetoacetyl-CoA thiolase (EC 2.3.1.9) | 1-10 |
| 3-Hydroxybutyryl-CoA dehydrogenase (EC 1.1.1.35 and/or EC 1.1.1.157) | 1-10 |
| Enoyl-CoA hydratase (EC 4.1.1.55 and/or EC 4.2.1.17) | 1-10 |
| Butyryl-CoA dehydrogenase (EC 1.3.1.44 EC 1.3.1.86 and/or 1.3.8.1) | 1-10 |
| Butyraldehyde dehydrogenase (EC 1.2.1.57 and/or EC 1.2.1.10) | 1-10 |
| Alcohol dehydrogenase (EC 1.1.1.1 and/or 1.1.1.2) | 1-10 |

Considering a system without regeneration of NADH, the theoretical stoichiometric balance indicates that to transform 19.55 g of pyruvate (equivalent to 20 g of lactate) to 8.22 g of butanol, 147.8 g of NADH and 170.5 g CoA would be needed. However, by implementing a regeneration system of NAD (P)$^+$/NAD (P) H and/or acetyl-CoA/CoA, as proposed in the present invention, 0.1 g of NAD (P)$^+$ alone was required and 0.1 g of CoA to transform 20 g lactate into 8.22 g butanol.

This shows that butanol production from lactate in a batch process, coupling the regeneration system NAD (P)$^+$/NAD (P) H and/or acetyl-CoA/CoA is possible.

Example 3. Enzymatic production of butanol from lactate, coupled to the regeneration system NAD (P)$^+$/NAD (P) H and/or acetyl-CoA/CoA in a continuous process.

This example is intended to demonstrate the concept of regeneration of NAD (P)$^+$/NAD (P) H and/or regeneration of acetyl-CoA/CoA in a continuous process, when the enzymes lactate dehydrogenase (EC 1.1.1.27 and/or EC 1.1.1.28) pyruvate formate-lyase (EC 2.3.1.54), formate dehydrogenase (EC 1.2.1.43), acetoacetyl-CoA thiolase (EC 2.3.1.9), 3-hydroxybutyryl-CoA dehydrogenase (EC 1.1.1.35 and/or EC 1.1.1.157), enoyl-CoA hydratase (EC 4.1.1.55 and/or EC 4.2.1.17), butyryl-CoA dehydrogenase (EC 1.3.1.44, EC 1.3.1.86 and/or 1.3.8.1), butanal dehydrogenase (EC 1.2.1.57 and/or EC 1.2.1.10), alcohol dehydrogenase (EC 1.1.1.1 and/or EC 1.1.1.2) or any of its analogs are used, according to the following reactions:

Conversion reaction of lactate to pyruvate. In this reaction two molecules of NAD (P) H are formed from two molecules of NAD (P)$^+$, with the transformation of two molecules of lactate into two molecules of pyruvate, this reaction can be performed using enzymes lactate dehydrogenase (EC 1.1.1.27 and/or EC 1.1.1.28) or any of its analogs:

$$2C_3H_6O_3 + 2NAD(P)^+ \Longrightarrow 2C_3H_4O_3 + 2NAD(P)H + 2H^+ \quad (10)$$

Conversion reaction of pyruvate to acetyl-CoA. In this reaction two pyruvate molecules are transformed into two molecules of acetyl-CoA, this reaction can be carried out using pyruvate formate-lyase enzyme (EC 2.3.1.54) or its analogues:

$$2C_3H_4O_3 + 2CoA \Longrightarrow 2C_{23}H_{38}N_7O_{17}P_3S + 2CH_2O_2 \quad (11)$$

Conversion reaction of formate to $CO_2$. In this reaction two formate molecules are transformed into two molecules of $CO_2$ using two molecules of NAD (P)$^+$, this reaction can be carried out using the enzyme formate dehydrogenase (EC 1.2.1.43) or its analogues:

$$2CH_2O_2 + 2NAD(P)^+ \Longrightarrow 2CO_2 + 2NAD(P)H + 2H^+ \quad (12)$$

Conversion reaction of acetyl-CoA into acetoacetyl-CoA. In this reaction two molecules of acetyl-CoA are converted in a molecule of acetoacetyl-CoA, this reaction can be carried out using acetoacetyl-CoA thiolase enzyme (EC 2.3.1.9) or its analogues:

$$2C_{23}H_{38}N_7O_{17}P_3S \Longrightarrow C_{25}H_{40}N_7O_{18}P_3S + CoA \quad (13)$$

Conversion reaction of acetoacetyl-CoA to 3-hydroxybutyryl-in CoA. In this reaction one molecule of NAD (P)+ is formed from one molecule of NAD (P) H, with the transformation of a molecule of acetoacetyl-CoA in a molecule of 3-hydroxybutyryl-CoA, this reaction can be carried out using hydroxybutyryl-3-CoA dehydrogenase (EC 1.1.1.35 and/or EC 1.1.1.157) or its analogs:

$$C_{25}H_{40}N_7O_{18}P_3S + NAD(P)H + H^+ \Longrightarrow C_{25}H_{42}N_7O_{18}P_3S + NAD(P)^+ \quad (14)$$

Conversion reaction of 3-hydroxybutyryl-CoA to crotonyl-CoA. In this reaction one molecule of 3-hydroxybutyryl-CoA becomes a molecule of crotonyl-CoA and water, this reaction can be carried out using enoyl-CoA hydratase enzyme (EC 4.1.1.55 and/or EC 4.2.1.17) or its analogs:

$$C_{25}H_{42}N_7O_{18}P_3S \Longrightarrow C_{25}H_{40}N_7O_{17}P_3S + H_2O \quad (15)$$

Conversion reaction of crotonyl-CoA to butanoyl-CoA. In this reaction one molecule of NAD (P)$^+$ is formed from one molecule of NAD (P) H, with the transformation of a molecule of crotonyl-CoA in a molecule butanoyl-CoA, this reaction can be carried out using butyryl-CoA dehydrogenase (EC 1.3.1.44, EC 1.3.1.86 and/or 1.3.8.1) or any of its analogs:

$$C_{25}H_{40}N_7O_{17}P_3S + NAD(P)H + H^+ \Longrightarrow C_{25}H_{42}N_7O_{17}P_3S + NAD(P)^+ \quad (16)$$

Conversion reaction of butanoyl-CoA to butanal. In this reaction a molecule of NAD(P)+ is formed from one molecule of NAD(P)H, with the transformation of a molecule butanoyl-CoA in a molecule of butanal, this reaction can be carried out using enzyme butanal dehydrogenase (EC 1.2.1.57 and/or EC 1.2.1.10) or any of its analogs:

$$C_{25}H_{42}N_7O_{17}P_3S + NAD(P)H + H^+ \Longrightarrow C_4H_8O + +NAD(P)^+ + CoA \quad (17)$$

Conversion reaction of butanal to butanol. In this reaction one molecule of NAD (P)$^+$ is formed from one molecule of NAD (P) H, with the formation of one molecule of butanol from a molecule butanal, this reaction can be performed using enzyme Alcohol dehydrogenase (EC 1.1.1.1 and/or EC 1.1.1.2):

$$C_4H_8O + NAD(P)H + H^+ \Longrightarrow C_4H_{10}O + NAD(P)^+ \quad (18)$$

From the above equations, the overall stoichiometric equation multi-enzymatic system has no loss or gain of NAD (P)+, NAD (P) H, CoA and/or acetyl-CoA, so that the overall reaction results in the use of two molecules of lactate to produce a molecule of butanol, obtaining an efficiency of 100% conversion according to the following reaction:

$$2C_3H_6O_3 ==> C_4H_{10}O + 2CO_2 + H_2O \tag{19}$$

Transforming lactate into butanol was carried out in a continuous reactor using free enzymes. The reaction mixture was formulated with the enzyme mixture (Table 35), cofactors and coenzymes (at the concentrations described in the prior art), lactic acid and NAD (P)+. The operating conditions of the reactor are shown in Table 36. The reactor inlet stream and reactor outlet stream were operated at the same flow rate, to have a continuous process.

Figure 3:
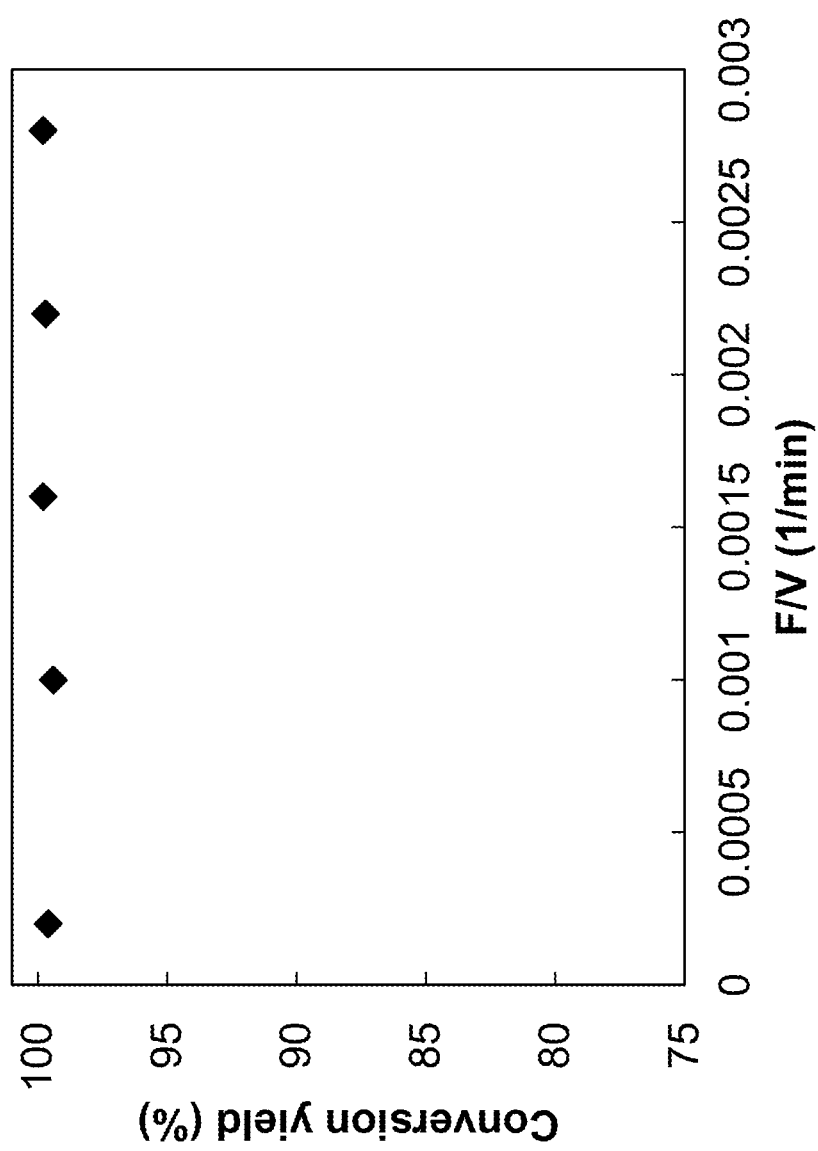
FIG. 3 shows a graph illustrating the behavior of the method of continuous production of butanol in a reactor CSTR.

In FIG. 3 some results from different conditions carried out in mechanically stirred reactor (CSTR) for the continuous process, corresponding to an initial lactate concentration 200 g/L and NAD (P)+ 1 g/L. The concentration of each of the enzymes in the reaction mixture was adjusted to 1 g/L. For all these operating conditions a volume 50 L was used, varying flow conditions.

TABLE 35

Enzymes used to formulate the enzyme mixture to produce butanol from lactate in a continuous process.

| Enzyme | Concentration in the enzyme mixture (g/L) |
| --- | --- |
| Lactate dehydrogenase (EC 1.1.1.27 and/or EC 1.1.1.28) | 1-10 |
| Pyruvate formate-lyase (EC 2.3.1.54) | 1-10 |
| Formate dehydrogenase (EC 1.2.1.43) | 1-10 |
| Acetoacetyl-CoA thiolase (EC 2.3.1.9) | 1-10 |
| 3-Hydroxybutyryl-CoA dehydrogenase (EC 1.1.1.35 and/or EC 1.1.1.157) | 1-10 |
| Enoyl-CoA hydratase (EC 4.1.1.55 and/or EC 4.2.1.17) | 1-10 |
| Butyryl-CoA dehydrogenase (EC 1.3.1.44 EC 1.3.1.86 and/or 1.3.8.1) | 1-10 |
| Butyraldehyde dehydrogenase (EC 1.2.1.57 and/or EC1.2.1.10) | 1-10 |
| Alcohol dehydrogenase (EC 1.1.1.1 and/or 1.1.1.2) | 1-10 |

TABLE 36

Reactor operating conditions for the production of butanol from lactate.

| Variable | Interval |
| --- | --- |
| Operating volume (L) | 1-100 |
| Lactate (g/L) | 1-300 |
| Temperature (° C.) | 20-37 |
| pH | 6-8 |
| NAD (P)+ (g/L) | 0.01-10 |
| CoA (g/L) | 0.01-10 |

The reaction was initiated in the same way as in the batch process (see Example 2), immediately after the addition and removal began, continuously, from the reaction medium.

The output stream of the reactor was coupled to a membrane system that separated enzymes, cofactors and coenzymes, and butanol. Stream of enzymes, cofactors and coenzymes was recirculated to the reactor.

In all the conditions listed in Tables 35 and 36 the evolution of reaction intermediates in the output stream of the reactor was monitored. The evolution of NAD(P)H was measured on a Cary-60 spectrophotometer at a wavelength of 340 nm. Lactate and butanol were measured by HPLC with refractive index detector using a Rezex ROA-organic acids H+ column.

As shown in FIG. 3, the conversion efficiency did not change relative to the flow condition and was close to 100%. In the same manner as in Example 2, it was demonstrated that the enzymatic production of butanol from lactate, coupled with the regeneration system of NAD (P)+/NAD (P) H and/or acetyl-CoA/CoA is possible, in the case of this example, using only 1 g/L NADP+ and 1 g/L CoA to transform 200 g/L lactate with a continuous process.

It is noteworthy that for other conditions shown in Tables 35 and 36 very similar conversion efficiencies were obtained.

Example 4. Enzymatic production of butanol from lactate, coupled to the regeneration system NAD (P)+/NADH and/or acetyl-CoA/CoA in a continuous process using immobilized enzymes.

This example is intended to demonstrate the concept of regeneration of NAD (P)+/NAD (P) H and/or regeneration of acetyl-CoA/CoA in a continuous process using immobilized enzymes, where the enzymes lactate dehydrogenase are used (EC 1.1.1.27 and/or EC 1.1.1.28), acetolactate synthase (EC 2.2.1.6), keto acid reductoisomerase (EC 1.1.1.86), dihydroxy acid dehydratase (EC 4.2.1.9), 2-oxoisovalerate dehydrogenase (EC 1.2.1.25 and/or EC 1.2.4.4), isobutyryl-CoA mutase (EC 5.4.99.13), butanal dehydrogenase (EC 1.2.1.57 and/or EC 1.2.1.10), alcohol dehydrogenase (EC 1.1.1.1 and/or EC 1.1.1.2), or its analogs, according to the following reactions:

Conversion reaction of lactate to pyruvate. In this reaction two molecules of NAD (P) H are formed from two molecules of NAD (P)+, with the transformation of two molecules of lactate into two molecules of pyruvate, this reaction can be performed using enzymes lactate dehydrogenase (EC 1.1.1.27 and/or EC 1.1.1.28) or any of its analogs:

$$2C_3H_6O_3 + 2NAD(P)^+ ==> 2C_3H_4O_3 + 2NAD(P)H + 2H^+ \tag{20}$$

Conversion reaction of pyruvate to acetolactate. In this reaction two pyruvate molecules are transformed into a molecule of acetolactate, this reaction can be carried out using ketolactate synthase enzyme (EC 2.2.1.6) or its analogues:

$$2C_3H_4O_3 ==> C_5H_8O_4 + CO_2 \tag{21}$$

Conversion reaction of acetolactate to 2,3-dihydroxyvalerate. In this reaction a molecule acetolactate becomes one molecule of 2,3-dihydroxyvalerate using a molecule of NAD (P)+, this reaction can be carried out using ketoacid reductoisomerase enzyme (EC 1.1.1.86) or its analogs:

$$C_5H_8O_4 + NAD(P)H + H^+ ==> C_5H_{10}O_4 + NAD(P)^+ \tag{22}$$

Conversion reaction of 2,3-dihydroxyvalerate to ketoisovalerate. In this reaction one molecule of 2,3-dihydroxyvalerate is transformed to ketoisovalerate molecule and a water molecule, this reaction can be carried out using dihydroxyacid dehydratase (EC 4.2.1.9) or its analogues:

$$C_5H_{10}O_4 ==> C_5H_8O_3 + H_2O \tag{23}$$

Conversion reaction of ketoisovalerate to isobutyryl-CoA. In this reaction one molecule of NAD(P)H is formed from one molecule of NAD (P)+, with the transformation of a molecule ketoisovalerate into a molecule of isobutyryl-CoA, this reaction can be performed using enzyme 2-oxoisovalerato dehydrogenase (EC 1.2.1.25 and/or EC 1.2.4.4) or any of its analogs:

$$C_5H_8O_3+CoA+NAD(P)^+ ==> C_{25}H_{42}N_7O_{17}P_3S+NAD(P)H+H^++CO_2 \quad (24)$$

Conversion reaction of isobutyryl-CoA to butyryl-CoA. In this reaction one molecule of isobutyryl-CoA is converted into a butyryl-CoA molecule, this reaction can be carried out using isobutyryl-CoA mutase enzyme (EC 5.4.99.13) or its analogues:

$$(CH_3)_2CHCOSCoA ==> CH_3(CH_2)_2COSCoA \quad (25)$$

Conversion reaction of butyryl-CoA to butanal. In this reaction a molecule of NAD (P)+ is formed from one molecule of NAD (P) H, with the transformation of a molecule butanoyl-CoA into a molecule of butanal, this reaction can be carried out using butanal dehydrogenase enzyme (EC 1.2.1.57 and/or EC 1.2.1.10) or any of its analogs:

$$C_{25}H_{42}N_7O_{17}P_3S+NAD(P)H+H^+ ==> C_4H_8O+NAD(P)^++CoA \quad (26)$$

Conversion reaction of butanal to butanol. In this reaction one molecule of NAD (P)+ is formed from one molecule of NAD (P) H, with the formation of one molecule of butanol from a molecule of butanal, this reaction can be performed using enzyme Alcohol dehydrogenase (EC 1.1.1.1 and/or EC 1.1.1.2):

$$C_4H_8O+NAD(P)H+H^+ ==> C_4H_{10}O+NAD(P)^+ \quad (27)$$

From the above equations, the overall stoichiometric equation multi-enzymatic system has no loss or gain of NAD (P)+, NAD (P) H, CoA and/or acetyl-CoA, so that the overall reaction results in the use of two molecules of lactate to produce a molecule of butanol, obtaining an efficiency of 100% conversion according to the following reaction:

$$2C_3H_6O_3 ==> C_4H_{10}O+2CO_2+H_2O \quad (28)$$

Butanol production in continuous form from lactate was carried out in a reactor immobilizing each enzyme or enzyme mixture (Table 37) in different media (Table 18), varying the amounts of immobilized protein. The operating conditions which were used are shown in Table 38. The reaction mixture was formulated by mixing coenzymes (at the concentrations described in the prior art) immobilized enzymes (Table 38), cofactors and lactic acid and NAD (P)+.

TABLE 37

Enzymes used to formulate the enzyme mixture to produce butanol from lactate in a continuous process with immobilized enzymes.

| Enzyme | Amount of enzyme by support amount (g/g) |
|---|---|
| Lactate dehydrogenase (EC 1.1.1.27 and/or EC 1.1.1.28) | 0.001 to 0.2 |
| Acetolactate synthase (EC 2.2.1.6) | 0.001 to 0.2 |
| Keto acid reductoisomerase (EC 1.1.1.86) | 0.001 to 0.2 |
| Dihydroxy acid dehydratase (EC 4.2.1.9) | 0.001 to 0.2 |
| 2-Oxoisovalerate dehydrogenase (EC 1.2.1.25 and/or EC 1.2.4.4) | 0.001 to 0.2 |
| Isobutyryl-CoA mutase (EC 5.4.99.13) | 0.001 to 0.2 |
| Butyraldehyde dehydrogenase (EC 1.2.1.57 and/or EC 1.2.1.10) | 0.001 to 0.2 |
| Alcohol dehydrogenase (EC 1.1.1.1 and/or 1.1.1.2) | 0.001 to 0.2 |

TABLE 38

Operating conditions of the continuous reactor with immobilized for processing enzymes lactate butanol.

| Reactor volume (L) | 1-100 |
|---|---|
| Amount of immobilized enzyme (g/g). | 0001-0.2 |
| Lactate (g/L) | 1-300 |
| Temperature (° C.) | 20-37 |
| pH | 6-8 |
| NAD (P)+ (g/L) | 0.01-10 |
| CoA (g/L) | 0.01-10 |

The output current of the reactor was coupled to a reverse osmosis system that can recirculate a mixture of cofactors and coenzymes to the reactor and/or mixing tank. The initial concentration of NAD (P)+ was 0.1 g/L, while the lactate concentration to the reactor inlet was varied according to Table 38. In all the conditions listed in Tables 37 and 38, the evolution of reaction intermediates along the tubular reactor was monitored. Changes in the NAD (P) H were measured on a Cary-60 spectrophotometer at a wavelength of 340 nm. Lactate and butanol were measured by HPLC with refractive index detector using a Rezex ROA-organic acids H+ column.

Figure 4:
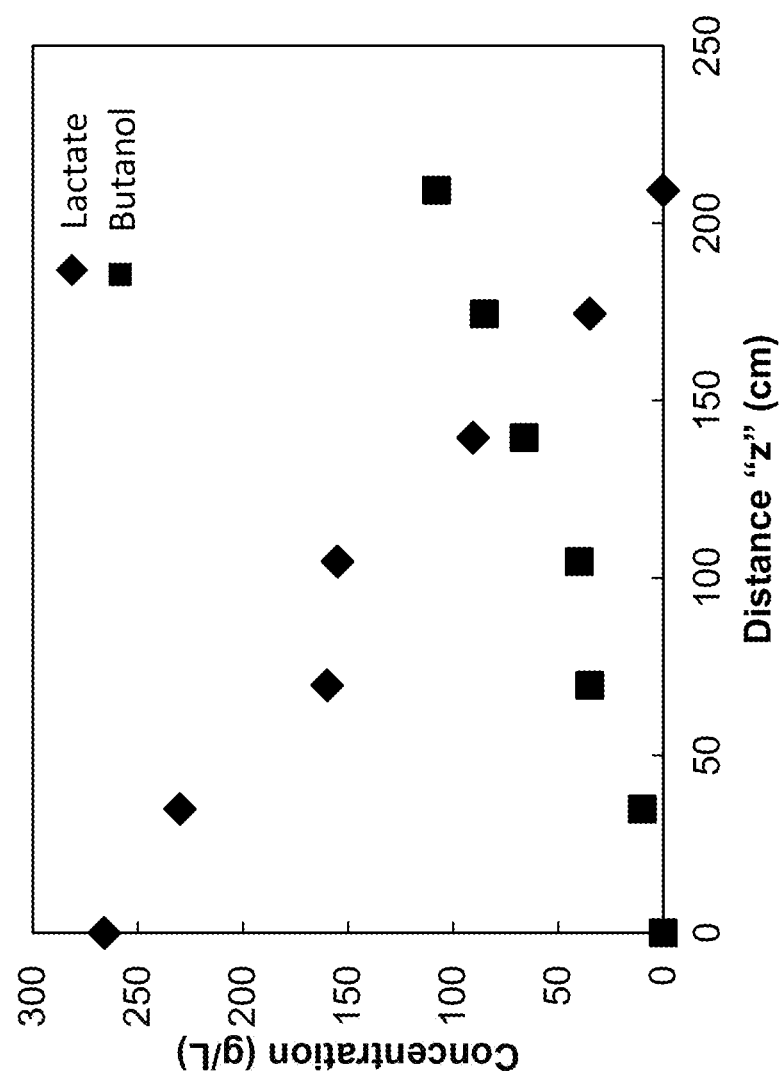
FIG. 4 shows a graph illustrating the behavior of the method of continuous production of butanol (along z axis) of a reactor PBR.

In FIG. 4 some results from different conditions made for continuous process using immobilized enzymes packed in a tubular reactor are shown. For all these conditions a trading volume 50 L was used, varying the conditions of feed flow, with a concentration of L-lactate to input 264 g/L and NAD (P)+0.1 g/L. The amount of each of the enzymes by support amount was adjusted to 0.01 g/g.

For this particular case, the reaction began when the mixture of cofactors, coenzymes, lactate and NAD (P)+ entered the packed reactor.

As shown in FIG. 4, lactate was transformed in butanol, under pressure through the packed tubular reactor, until 100% conversion efficiency. The same happened with the different operating conditions mentioned in the Tables 37 and 38. In the same way as in Examples 2 and 3, it was shown that the coupling of the enzymatic production of butanol from lactate, with the regeneration system NAD (P)+/NAD (P) H and/or of acetylCoA/CoA is possible using only 0.1 g/L NAD (P)+ to convert 264 g/L lactate 108 g/L butanol.

REFERENCES

Atsumi S, Li Z, J C Liao. (2009). Acetolactate synthase from *Bacillus subtilis* servesas 2-ketoisovalerate decarboxylase for butanol biosynthesis in *Escherichia coli*. Appl Environ Microbiol. 75 (19): 6306-6311.

Atsumi S, T Y Wu, Eckl M S, S D Hawkins, Buelter T, Liao J C (2010) butanol biosynthetic pathway Engineering the *Escherichia coli* by comparison of three aldehyde reductase/Alcohol dehydrogenase genes. Appl Microbiol Biotechnol. 85 (3): 651-657.

Z Barak, Chipman D M, Gollop N. (1987). Physiological Implications of the specificity of acetohydroxy acid synthase isozymes of enteric bacteria. J Bacteriol. 169 (8): 3750-3756.

Bastian S, Liu X, Meyerowitz J T Snow C D, Chen M M, Arnold F H. (2011). Engineered ketol-acid reductoisomerase and Alcohol dehydrogenase 2-methylpropan-1-ol enable anaerobic production at theoretical yield in *Escherichia coli*. Metab Eng 13 (3): 345-352.

Berezina O V, Zakharova N V, Yarotsky C V, V V Zverlov. (2012). Microbial Producers of butanol. Appl. Biochem. Microbiol. 48 (7): 625-638.

Cetinel S, Caliskan H B, Yucesoy D T, Donatan A S, Yuca And Urged M, Karaguler N G, Tamerler C. (2013) self-addressable immobilization of lactate dehydrogenase across multiple length scales. J. Biotechnol 8 (2): 262-272.

Square M, Fernandez de Palencia P, C Pelaez, Requena and molecular T. Biochemical characterization of alpha-ketoisovalerate decarboxylase, an enzyme involved in the formation of aldehydes from amino acids by *Lactococcus lactis*. (2004). FEMS Microbiol Lett. 238 (2): 367-74.

J R Dickinson, S J Harrison, M J Hewlins. (1998) An investigation of the metabolism of valine to isobutyl alcohol, *Saccharomyces cerevisiae* in J Biol Chem 273 (40): 25751-25756.

Flint D H, M H Emptage, Finnegan M G, Fu W, Johnson M K. (1993). The role and properties of the iron-sulfur cluster in *Escherichia coli* dihydroxy-acid dehydratase. J Biol Chem 268 (20). 14732-14742.

Fukui T, N Shiomi, Doi Y. (1998). Expression and Characterization of (R)—specific Enoyl Coenzyme A hydratase Polyhydroxyalkanoate Involved in the Biosynthesis by *Aeromonas caviae*. J. Bacteriol. 180 (3): 667-673.

Michael R. Green, Joseph Sambrook. (2012). Molecular Cloning: A Laboratory Manual. Cold Spring Harbor Laboratory Press; 4th edition.

Hatrongjit R, Packdibamrung K A. (2010) novel NADP+ dependent dehydrogenase from *Burkholderia* formed stabilis 15516: Screening, purification and characterization. Enzyme Microb. Technol. 46: 557-561.

W D Holtzclaw, Chapman L F. (1975). Degradative acetolactate synthase of *Bacillus subtilis*: purification and properties. J Bacteriol. 121 (3): 917-922.

Hakozaki M I, Ono K, Suzuki T, Hata H, Mori T, Kochi H. (2002). Characterization of rainbow trout alpha-keto acid branched-chain dehydrogenase complex: inter-domain segments of the E2 component Affect the overall activity. Comp Biochem Physiol B Biochem Mol Biol 132 (2): 433-42.

Hu K, Zhao M, Zhang T, Zha M, C Zhong, Jiang Y, Ding J. (2013) Structures of trans-2-enoyl-CoA reductases from *Clostridium acetobutylicum* and *denticola Treponema*: insights into the substrate specificity and the catalytic mechanism J. Biochem 449 (1): 79-89.

W Huth, Jonas R, Wunderlich I, W. Seubert (1975). On the mechanism of ketogenesis and Its control. Purification, kinetic mechanism and regulation of different forms of mitochondrial acetoacetyl-CoA thiolases from ox liver. Eur. J. Biochem. 59: 475-489.

D T Jones, Woods D R. (1986). Acetone-butanol fermentation revisited. Microbiol. Rev. 50 (4): 484-524.

Kim S, Gu S A, Kim Y H, Kim K J (2014) Crystal structure and thermodynamic properties of d-lactate dehydrogenase from *Lactobacillus jensenii*. Int J Biol Macromol. 68: 151-7.

Li S, Wen J, Jia X. (2011) Engineering *Bacillus subtilis* for butanol production by heterologous Ehrlich pathway construction and the biosynthetic pathway precursor 2-ketoisovalerate overexpression. Appl Microbiol Biotechnol. 91 (3): 577-589.

Lia J, Tana S N, Ge H. (nineteen ninety six). Silica sol-gel immobilized Amperometric biosensor for hydrogene peroxide Analytica Chimica Acta 335 (1-2): 137-145

Liu B, R Hu, Deng J. (1997). Characterization of immobilization of an enzyme in a modified and zeolite matrix and Its application to an Amperometric glucose biosensor. Anal Chem 69 (13): 2343-2348.

V K Madan, Hillmer P, Gottschalk G. (1973) Purification and properties of NADP-dependent L(+)-3-hydroxybutyryl-CoA dehydrogenase from *Clostridium kluyveri*. Eur. J. Biochem. 32: 51-56.

Nemeria N, Yan Y, Zhang Z, Brown A M, Arjunan P, Furey W, Guest J R, F Jordan (2001). *Escherichia coli* Inhibition of the Pyruvate Dehydrogenase Complex and Its Subunit E1 Tyrosine 177 Variants by 2-Thiazolone Thiamin and Thiamin 2-Thiothiazolone diphosphates: Evidence for reversible tight-binding inhibition. J Biol Chem 276: 45969-45978.

Palosaari N R, Rogers P. (1988). Purification and properties of the inducible coenzyme A dehydrogenase-linked from *Clostridium acetobutylicum* butyraldehyde. J. Bacteriol. 170: 2971-2976

M J Rane, Calvo K C. (1997). Reversal of the nucleotide specificity of ketol acid reductoisomerase by site-directed mutagenesis Identifies the NADPH binding site. Arch Biochem Biophys. 338 (1): 83-89.

Ratnatilleke A, Vrijbloed J W, Robinson J A. (1999). Cloning and sequencing of the coenzyme B (12)-binding domain of Isobutyryl-CoA mutase from *Streptomyces cinnamonensis*, reconstitution of mutase activity, and characterization of the recombinant enzyme produced in *Escherichia coli*. J Biol Chem 274: 31679-31685.

Takahashi S, Abbe K, Yamada T, (1982). Purification of pyruvate formed-lyase from *Streptococcus mutans* and Its regulatory properties. J. Bacteriol. 149: 1034-1040.

S F Torabi, Khajeh K, Ghasempur S, N Ghaemi, Siadat S O (2007). Covalent attachment of cholesterol oxidase and horseradish peroxidase on perlite through silanization: activity, stability and co-immobilization. J Biotechnol. 131 (2): 111-20.

Wona K, Kima S, Kima K J, Park H W, Moona S J (2005). Optimization of lipase entrapment in Ca-alginate gel beads. Process Biochem. 40: 2149-2154

Obviously, numerous modifications and variations of the present invention are possible in light of the above teachings. It is therefore to be understood that within the scope of the appended claims, the invention may be practiced otherwise than as specifically described herein.

The invention claimed is:

1. A process for producing n-butanol, comprising:
A) mixing water, lactate, an enzyme mixture, at least one cofactor and at least one coenzyme, to prepare a reaction mixture, wherein the enzyme mixture comprises:
lactate dehydrogenase EC 1.1.1.27 and/or EC 1.1.1.28,
pyruvate dehydrogenase EC 1.2.1.51, EC 1.2.4.1, EC 2.3.1.12 and/or EC 1.8.1.4, acetoacetyl-CoA thiolase EC 2.3.1.9,
3-hydroxybutyryl-CoA dehydrogenase EC 1.1.1.35 and/or EC 1.1 0.1.157,
enoyl-CoA hydratase EC 4.1.1.55 and/or EC 4.2.1.17,
butyryl-CoA dehydrogenase EC 1.3.1.44, EC 1.3.1.86 and/or 1.3.8.1,
butanal dehydrogenase EC 1.2.1.57 and/or EC 1.2.1.10,
alcohol dehydrogenase EC 1.1.1.1 and/or EC 1.1.1.2,
pyruvate formate lyase EC 2.3.1.54,
formate dehydrogenase EC 1.2.1.43,
acetolactate synthase EC 2.2.1.6,
ketoacid reductoisomerase EC 1.1.1.86,
dihydroxy acid dehydratase EC 4.2.1.9,
2-oxoisovalerato dehydrogenase EC 1.2.1.25 and/or EC 1.2.4.4, and
isobutyryl-CoA mutase EC 5.4.99.13;

B) catalytically reacting the reaction mixture at a temperature of from 15 to 37° C. for an amount of time sufficient to cause conversion of lactate into n-butanol; and C) separating the n-butanol from a reactant obtained by the catalytic conversions in B), wherein the conversion of lactate into n-butanol in B) is conducted with no overall loss or gain of Nicotinamide Adenine Dinucleotide (NAD+) and Reduced Nicotinamide Adenine Dinucleotide (NADH) and/or Nicotinamide Adenine Dinucleotide Phosphate (NADP+) and Reduced Nicotinamide Adenine Dinucleotide Phosphate (NADPH), and less than a stoichiometric amount of NAD+ and/or NADP+ is employed to obtain a n-butanol from lactate with a conversion efficiency of 98 to 100%.

2. The process of claim 1, wherein, in B):
the lactate is converted into pyruvate;
the pyruvate is converted into acetyl-CoA;
the acetyl-CoA is converted into acetoacetyl-CoA;
the acetoacetyl-CoA is converted into 3-hydroxybutyryl-CoA;
the 3-hydroxybutyryl-CoA is converted into crotonyl-CoA;
the crotonyl-CoA is converted into butyryl-CoA;
the butyryl-CoA is converted into n-butanal; and
the n-butanal is converted into n-butanol.

3. The process of claim 1, wherein, in B):
the lactate is converted into pyruvate;
the pyruvate is converted to acetyl-CoA and formate;
the formate is converted into $CO_2$;
the acetyl-CoA is converted into acetoacetyl-CoA;
the acetoacetyl-CoA is converted into 3-hydroxybutyryl-CoA;
the 3-hydroxybutyryl-CoA is converted into butyryl-CoA;
the butyryl-CoA is converted into n-butanal; and
the n-butanal is converted into n-butanol.

4. The process of claim 1, wherein, in B):
the lactate is converted into pyruvate;
the pyruvate is converted into acetolactate;
the acetolactate is converted into 2,3-dihydroxyvalerate;
the 2,3-dihydroxyvalerate is converted into ketoisovalerate;
the ketoisovalerate is converted into isobutyryl-CoA;
the isobutyryl-CoA is converted into butyryl-CoA;
the butyryl-CoA is converted into n-butanal; and
the n-butanal is converted into n-butanol.

5. The process of claim 1, wherein:
the enzyme mixture is prepared in a container before or in step A).

6. The process of claim 1, wherein the process is carried out continuously, semicontinuously or batch manner.

7. The process of claim 1, wherein the lactate is L-lactate, D-lactate or a mixture of both.

8. The process of claim 1, wherein the lactate concentration in the reaction mixture is at least 1 g/L.

9. The process of claim 1, wherein at least one enzyme may be immobilized, entrapped, embedded, adhered, attached, secured, absorbed, adsorbed or otherwise attached or associated with a support.

10. The process of claim 9, wherein the support is at least one of the following: zeolite, activated carbon, acrylamide, agarose, silica gel, silica, alginate or methacrylate polymers.

11. The process of claim 1, wherein the concentration of enzymes in the enzyme mixture is higher than 0.001 g/L.

12. The process of claim 9, wherein the concentration of enzymes on the support is greater than 0.001 grams of enzyme per gram of support.

13. The process of claim 1, wherein the separation of n-butanol from the reaction mixture comprises:
separating the reactants obtained by the catalytic conversions in B) into a first stream and a second stream, wherein the first stream comprises n-butanol and water, and the second stream comprises components different from n-butanol.

14. The process of claim 13, wherein the second stream is recycled or reused by mixing it with the reaction mixture in A), B), or both.

15. The process of claim 13, wherein, the separation is carried out to separate based on their physicochemical properties.

16. The process of claim 13, wherein the separation is carried out by membranes, distillation, evaporation, or a combination thereof.

17. The process of claim 5, wherein the container is a tube, a tank or a reactor or a combination thereof.

18. The process of claim 5, wherein the mixing is carried out by a method to allow interaction between at least one enzyme and the substrates and/or compounds.

19. The process of claim 5, wherein the mixing is carried out mechanically, pneumatically, hydraulically or by a combination thereof.

20. The process of claim 1, wherein the catalytic conversion in step B) is carried out in a container or a reactor to promote interactions between enzymes and substrates and/or compounds.

21. The process of claim 20, wherein the container or reactor is a stirred tank, a plug flow reactor, a fluidized bed reactor, a packed bed reactor, or any combination thereof.

22. The process of claim 20, wherein the catalytic conversions are carried out in a pH range of 5 to 10.

* * * * *